United States Patent
Hughes et al.

(10) Patent No.: US 10,893,371 B2
(45) Date of Patent: Jan. 12, 2021

(54) APPARATUS AND METHOD FOR TREATING A NEUROLOGICAL DISORDER OF THE AUDITORY SYSTEM

(71) Applicant: Neuromod Devices Limited, Dublin (IE)

(72) Inventors: Stephen Hughes, Dublin (IE); Ross O'Neill, Dublin (IE); Brendan Conlon, Dublin (IE); Caroline Hamilton, Dublin (IE); Shona D'Arcy, Dublin (IE)

(73) Assignee: Neuromod Devices Limited, Dublin (IE)

( * ) Notice: Subject to any disclaimer, the term of this patent is extended or adjusted under 35 U.S.C. 154(b) by 183 days.

(21) Appl. No.: 15/777,166

(22) PCT Filed: Nov. 15, 2016

(86) PCT No.: PCT/EP2016/077781
§ 371 (c)(1),
(2) Date: May 17, 2018

(87) PCT Pub. No.: WO2017/085083
PCT Pub. Date: May 26, 2017

(65) Prior Publication Data
US 2019/0387335 A1    Dec. 19, 2019

(30) Foreign Application Priority Data

Nov. 17, 2015  (EP) ..................................... 15195055
Nov. 17, 2015  (IE) ..................................... 20150407

(51) Int. Cl.
*H04R 25/00* (2006.01)
*A61N 1/05* (2006.01)
(Continued)

(52) U.S. Cl.
CPC ............. *H04R 25/75* (2013.01); *A61B 5/128* (2013.01); *A61N 1/0548* (2013.01); *A61N 1/361* (2013.01);
(Continued)

(58) Field of Classification Search
CPC ................ A61N 1/0456; A61N 1/0548; A61N 1/36014; A61N 1/36034; A61N 1/36139;
(Continued)

(56) References Cited

U.S. PATENT DOCUMENTS

2014/0275737 A1*  9/2014  Shore ................. A61N 1/36036
                                                       600/26

FOREIGN PATENT DOCUMENTS

EP            2842530         3/2015

* cited by examiner

*Primary Examiner* — Christine H Matthews
*Assistant Examiner* — Joshua Daryl D Lannu
(74) *Attorney, Agent, or Firm* — Schmeiser, Olsen & Watts LLP

(57) ABSTRACT

An apparatus for use in treating a neurological disorder of the auditory system, including a stimulus generation unit and a somatosensory stimulation unit. The stimulus generation unit operable to analyse an audio signal including a first component comprising a broadband or white noise component and a second component including a plurality of complex tone bursts, and generate a plurality of actuation signals representative of at least one of the first or second component of the audio signal and further to spectrally modify the audio signal to generate a binaural modified audio signal for delivery to a subject. The somatosensory stimulation unit includes: an array of stimulators to apply a somatosensory stimulation to the subject with the modified audio signal, and an input for receiving the plurality of actuation signals from the stimulus generation unit and
(Continued)

directing individual actuation signals in a predetermined pattern to individual stimulators in the array.

18 Claims, 13 Drawing Sheets

(51) Int. Cl.
*A61N 1/36* (2006.01)
*A61B 5/12* (2006.01)
(52) U.S. Cl.
CPC ...... *A61N 1/36139* (2013.01); *H04R 2460/13* (2013.01)
(58) Field of Classification Search
CPC ................ A61N 1/361; A61N 1/36036; H04R 2460/13; H04R 25/75; A61B 5/128; A61B 5/4833; A61B 5/4848; A61B 5/7455; A61M 2021/0027; A61M 2021/0072; A61M 21/02; A61F 11/04
See application file for complete search history.

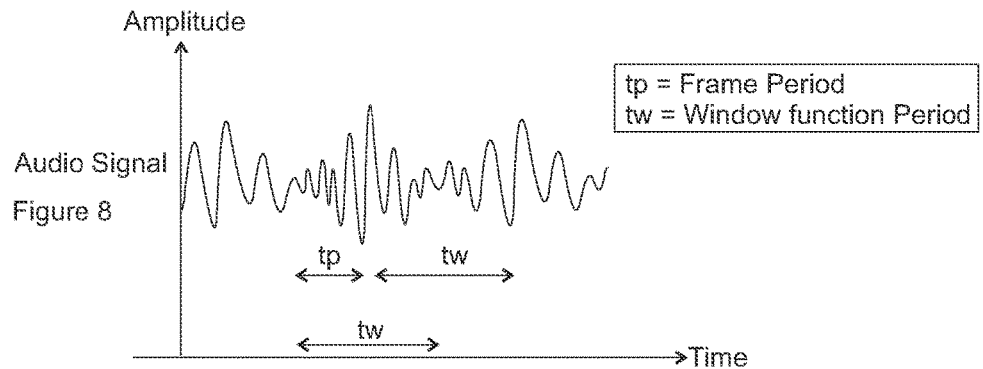
Audio Signal
Figure 8
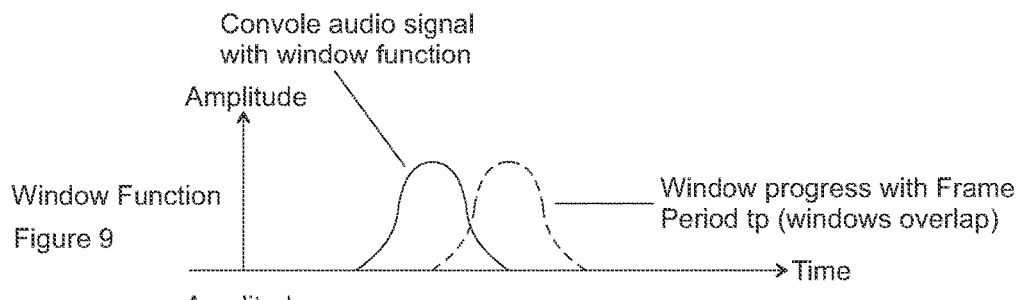
Window Function
Figure 9
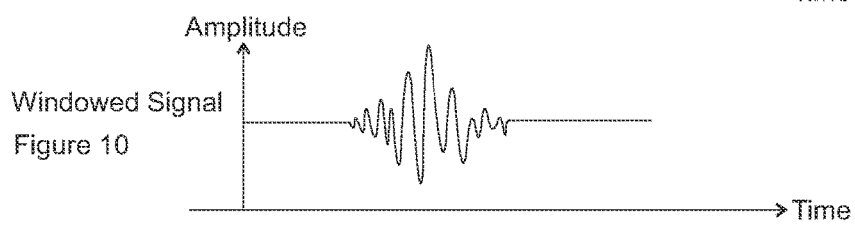
Windowed Signal
Figure 10
Audio frame transformed into the frequency domain
Figure 11
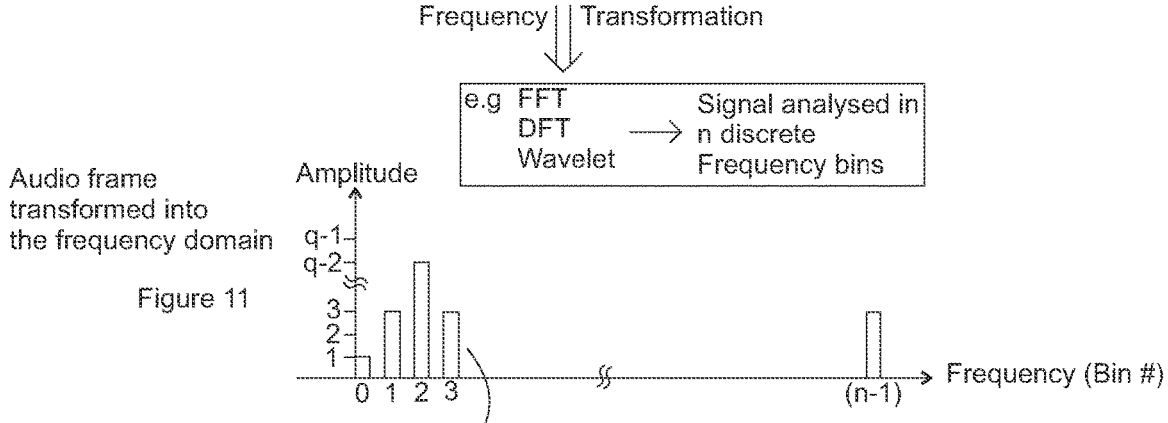

Figure 15: Average symptom scores over 10 weeks of treatment for MML and TLM (Units in dB HL) and THI

| Somatosensory Amplitude Setting | MB2 | | | MB1 | | |
|---|---|---|---|---|---|---|
| | Pulse Width [us] | Pulse Voltage [V] | Pulse Volt-seconds [Vus] | Pulse Width [us] | Pulse Voltage [V] | Pulse Volt-seconds [Vus] |
| 0 | 0 | 4.35 | 0 | 17.7 | 0 | 0 |
| 1 | 5 | 4.35 | 22 | 17.7 | 3 | 53 |
| 2 | 9 | 4.35 | 39 | 17.7 | 3.5 | 62 |
| 3 | 12 | 4.35 | 52 | 17.7 | 4 | 71 |
| 4 | 15 | 4.35 | 65 | 17.7 | 4.5 | 80 |
| 5 | 18 | 4.35 | 78 | 17.7 | 5 | 89 |
| 6 | 21 | 4.35 | 91 | 17.7 | 5.5 | 97 |
| 7 | 25 | 4.35 | 109 | 17.7 | 6 | 106 |
| 8 | 29 | 4.35 | 126 | 17.7 | 6.5 | 115 |
| 9 | 34 | 4.35 | 148 | 17.7 | 7 | 124 |
| 10 | 39 | 4.35 | 170 | 17.7 | 7.5 | 133 |
| 11 | 44 | 4.35 | 191 | 17.7 | 8 | 142 |
| 12 | 49 | 4.35 | 213 | 17.7 | 8.4 | 149 |
| 13 | 54 | 4.35 | 235 | 17.7 | 9.1 | 161 |
| 14 | 59 | 4.35 | 257 | 17.7 | 9.6 | 170 |
| 15 | 65 | 4.35 | 283 | 17.7 | 9.9 | 175 |
| 16 | 72 | 4.35 | 313 | 17.7 | 10.5 | 186 |
| 17 | 78 | 4.35 | 339 | 17.7 | 10.9 | 193 |
| 19 | 78 | 4.85 | 378 | | | |
| 20 | 78 | 5.35 | 417 | | | |
| 21 | 78 | 5.85 | 456 | | | |

FIG. 19

| Channel number | Filter centre freq. [Hz] | Filter Centre Freq. Period [ms] | Gammatone filter period (10x centre frequency period) [ms] | Analysis window length tf[x] [ms] | Refractory period [ms] | Analysis Window Shift Step [ms] | Max # pulses per second |
|---|---|---|---|---|---|---|---|
| 1 | 570 | 1.75 | 17.54 | 20.0 | 2.5 | 5.0 | 200 |
| 2 | 700 | 1.43 | 14.29 | 15.0 | 2.5 | 5.0 | 200 |
| 3 | 840 | 1.19 | 11.90 | 15.0 | 2.5 | 5.0 | 200 |
| 4 | 1000 | 1.00 | 10.00 | 10.0 | 2.5 | 5.0 | 200 |
| 5 | 1170 | 0.85 | 8.55 | 10.0 | 2.5 | 2.5 | 400 |
| 6 | 1370 | 0.73 | 7.30 | 7.5 | 2.5 | 2.5 | 400 |
| 7 | 1600 | 0.63 | 6.25 | 7.5 | 2.5 | 2.5 | 400 |
| 8 | 1850 | 0.54 | 5.41 | 7.5 | 2.5 | 2.5 | 400 |
| 9 | 2150 | 0.47 | 4.65 | 5.0 | 2.5 | 2.5 | 400 |
| 10 | 2500 | 0.40 | 4.00 | 5.0 | 2.5 | 2.5 | 400 |
| 11 | 2900 | 0.34 | 3.45 | 5.0 | 2.5 | 2.5 | 400 |
| 12 | 3400 | 0.29 | 2.94 | 5.0 | 2.5 | 2.5 | 400 |
| 13 | 4000 | 0.25 | 2.50 | 2.5 | 2.5 | 2.5 | 400 |
| 14 | 4800 | 0.21 | 2.08 | 2.5 | 2.5 | 2.5 | 400 |
| 15 | 5800 | 0.17 | 1.72 | 2.5 | 2.5 | 2.5 | 400 |
| 16 | 7000 | 0.14 | 1.43 | 2.5 | 2.5 | 2.5 | 400 |

FIG. 20

APPARATUS AND METHOD FOR TREATING A NEUROLOGICAL DISORDER OF THE AUDITORY SYSTEM

FIELD OF THE INVENTION

The present invention relates to the delivery of a bimodal stimulus to a subject suffering from a neurological disorder of the auditory system.

BACKGROUND TO THE INVENTION

Subjective tinnitus is an intrusive and debilitating condition, most commonly described as 'ringing in the ears' that significantly affects up to 5% of the global population. Many tinnitus sufferers report feeling distressed by their symptoms and report a resulting diminishment in their quality of life and that of their families. Patients find further frustration in a perceived lack of treatment options. Currently available treatments (discussed below) are limited, with the vast majority of patients being told there are no treatment options and that they should 'learn to live with their tinnitus'. This has resulted in widespread disillusionment with the clinical professions and pent up market demand for a viable treatment alternative. Leading tinnitus experts have acknowledged that current treatments are ineffective and that there is a remaining unmet clinical need. They have also stressed that a treatment that produced even a small but significant effect would have an enormous therapeutic impact on this huge and growing underserviced market. Both pharmacologic and non-pharmacologic treatments are currently used to manage the symptoms of tinnitus. These range from off-label drugs, such as Serc, through different forms of psychological counselling, including Tinnitus Retraining Therapy (TRT) and Cognitive Behavioural Therapy (CBT), to medical devices, such as Hearing Aids, Noise-maskers and Electrical Stimulators. Current therapies tend to provide only temporary symptomatic relief and are generally chosen based on the severity of the condition. The benefit and limitations of these treatments have been the subject of a number of review articles. Pharmacological treatments include; antidepressants, vasodilators, intravenous lidocaine, barbiturates, antihistamines, beta histamine, and benzodiazepines. However, it is preferable pharmacological treatments are used to treat coexisting symptoms such as depression and anxiety. Generally, the ineffectiveness of pharmacological treatments has been recognised and documented by leading tinnitus experts.

Tinnitus has a diverse range of etiologies but it is commonly accompanied by a high-frequency hearing loss, or sensorineural hearing loss (SNHL). There is a growing body of scientific evidence that hearing loss causes increased neural spontaneous and stimulus-driven excitability in the auditory brainstem and cortex, and that this increased activity is linked with the perception of the illusory sounds of tinnitus. Two recognised modalities may be stimulated in order to suppress this neuropathological hyperactivity:

Auditory Stimulation
Somatosensory Stimulation

EP2 842 530 A1 and EP2 658 491 A1 both combine auditory and somatosensory stimulation in the treatment of tinnitus. In applying multi-modal neuromodulation, it is theorised that stimulating the neural pathways of patients through both the somatic and auditory senses with the same information, may give increased benefit to the patient over time, as it may facilitate the brain to learn which part of the perceived sound is real, and which part is illusory (the pathological tinnitus). US2014/275737A1 discloses timed stimulation of both somatosensory system and auditory system to alter an individual's brain activity through spike timing dependent plasticity thereby reducing or removing tinnitus. Stimuli are generated and applied in an alternative mechanism to that disclosed in the present application. However, there is a need to provide an improved device which offers significant advantages in terms of performance and usability when compared with the prior art and the commercially available tinnitus treatments described above. The present invention solves this problem through an alternative transformation between the auditory and somatosensory stimulation.

SUMMARY OF THE INVENTION

There is described herein with reference to the appended claims an apparatus and method for use in treating a neurological disorder of the auditory system.

The apparatus, in accordance with an embodiment of the invention may comprise a stimulus generation unit and a somatosensory stimulation unit; the stimulus generation unit operable to analyse an audio signal, said audio signal comprising a first component comprising a broadband or white noise component and a second component comprising a plurality of complex tone bursts, and generate a plurality of actuation signals representative of at least one of the first or second component of said audio signal and further to spectrally modify said audio signal to generate a binaural modified audio signal for delivery to a subject; and wherein said somatosensory stimulation unit comprises: an array of stimulators each of which can be independently actuated to apply a somatosensory stimulation to the subject with the modified audio signal, and an input for receiving the plurality of actuation signals from said stimulus generation unit and directing individual actuation signals in a predetermined pattern to individual stimulators in the array, the stimulus generation unit being further configured to introduce a delay between the plurality of actuation signals representative of said audio signal and the binaural modified audio signal.

The introduction of a delay allows the optimisation of the treatment for the subject and further optimises the performance of a combined auditory and somatosensory treatment system.

The delay may be a fixed delay between −50 ms and +50 ms The delay between the modified audio signal and the plurality of actuation signals may be configured to vary randomly, said random delay having a probability distribution that is rectangular, with limits of up to +1-50 ms, or Gaussian, with standard deviation of up to +1-20 ms.

The stimulus generation unit may comprise an amplitude control for controlling an amplitude of the modified audio signal and an amplitude of the somatosensory stimulation.

Accordingly, the intensity of stimulation can be adjusted per patient and the treatment further optimised.

The amplitude control may be further operable to modulate the amplitude of the modified audio signal for an interval during a treatment session of the subject.

The amplitude control may be operable to ramp (decrescendo) an amplitude of the modified audio signal from a nominal level to a level commensurate with a hearing level of the subject for between 1 minutes and 5 minutes before the completion of the treatment session of the subject.

The stimulus generation unit may further comprise a band boost filter, calibrated in accordance with an audiogram of the subject and wherein the stimulus generation unit is operable to spectrally modify said audio signal by passing the audio signal through said band boost filter to produce said modified audio signal.

This further enhances the customisability of the system described herein.

The centre frequency of the band boost filter may be set to match the steepest roll off of the audiogram of the ipsilateral ear of the patient, wherein the half-power bandwidth of the band boost filter is between 0.5 and 1.5 octaves normalised to the centre frequency, and with a boost magnitude of at least 12 dB.

The stimulus generation unit may further comprise a filter that is based on the inverse of the audiogram of the subject in the ipsilateral ear and the filter is configured to compensate for deficits of at least 30 dB and operable in the range from 500 Hz to 16 kHz. Spectral modification may therefore be based on an inversion of an audiogram of the subject.

The array of stimulators may comprise an additional array comprising at least two stimulators, symmetrically arranged relative to the array of stimulators and configured to deliver a pseudo-stimulus to the subject. This pseudo stimulus further enhances the treatment as it contributes to providing a sensation of an effect to the patient. For example, this is useful where the primary stimulus channels deliver a weak or imperceptible somatosensory stimulus.

The array of stimulators may be used to deliver both the treatment stimulus and the pseudo stimulus. The treatment stimulus and the pseudo stimulus may be multiplexed in time with a mark:space ratio of pseudo to treatment stimulus of no more than 10%.

The somatosensory stimulation unit may be in the form of a body dimensioned to be applied trans-cutaneously or trans-mucosally on a nerve fibre of the subject.

The somatosensory stimulation may comprise a periodic pulse train having a pulse train with a pulse period less than a period of the nerve fibre to which the somatosensory stimulation unit is applied.

The somatosensory stimulation unit may be in the form of a body dimensioned to be applied to the mandibular branch or the lingual branch or the maxillary branch or the ophthalmic branch of the trigeminal nerve or to the accessory nerve or the cervical spinal nerves, C1 and C2.

The somatosensory unit may be in the form of a body dimensioned to be located on the tongue and wherein the array of stimulators may comprise a split array having an equal number of stimulators distributed along the medial line of the tongue and wherein the predetermined pattern comprises an ipsilateral mapping of the individual actuation signals with a dead band located along the medial line. This split array promotes neuroplasticity at the sub-cortical and cortical levels. This is more effective at driving plastic changes at the sub-cortical levels because the auditory stimulus for each side is matched to the ipsilateral somatosensory stimulus.

The somatosensory unit may be further dimensioned to provide a positioning aid for centring the device along the medial line.

The array of stimulators may be arranged in a raster pattern such as that shown in FIGS. 5 and 17 such that each stimulator in the raster pattern is arranged from lowest frequency bin to highest frequency bin, or the array of stimulators is arranged in a spiral pattern having a lowest frequency mapping on the inside of the spiral with the highest frequency on the outside of the spiral, or the array may be arranged such that the frequency bins corresponding to the highest deficit in the subject's hearing loss are located proximal to contact regions of highest somatosensory innervation density (for example towards the tip of the tongue for a tongue stimulator embodiment).

A further embodiment of the invention includes a method of treatment of a neurological disorder of the auditory system, comprising: analysing an audio signal, said audio signal comprising a first component comprising a spectral bandwidth that elicits the perception of an audio signal having a broadband or white noise component and a second component comprising a plurality of complex tone bursts, generating a plurality of actuation signals representative of said audio signal and independently actuating an array of stimulators to apply a somatosensory stimulation to a subject; and spectrally modifying said audio signal to generate a binaural modified audio signal for delivery to the subject; wherein the somatosensory stimulation and the modified audio signal are synchronously applied to the subject; and introducing a delay between the plurality of actuation signals representative of said audio signal and the binaural modified audio signal.

A further embodiment of the invention includes a device for treatment of a neurological disorder of the auditory system wherein the device is configured to analyse an audio signal, said audio signal comprising a first component comprising an audio signal having a broadband or white noise component and a second component comprising a plurality of complex tone bursts, generating a plurality of actuation signals representative of said audio signal and independently actuating an array of stimulators to apply a somatosensory stimulation to a subject; and spectrally modifying said audio signal to generate a binaural modified audio signal for delivery to the subject; wherein the somatosensory stimulation and the modified audio signal are synchronously applied to the subject; and introducing a delay between the plurality of actuation signals representative of said audio signal and the binaural modified audio signal.

BRIEF DESCRIPTION OF THE DRAWINGS

Various non-limiting embodiments of the technology described herein will not be described with specific reference to the following figures. It should be appreciated that the figures are not necessarily drawn to scale.

FIGS. 8 to 14 illustrate the transformation between audio and somatosensory stimulation and illustrate how one of the binaural channels is transformed for use in a split-array stimulator topology in accordance with an embodiment of the present invention.

FIG. 19 is a table showing electrical pulse parameters as a function of the global stimulus levels for the MB2 and MB1.

FIG. 20 is a table showing the optimum analysis window lengths for each listed frequency bin (filter) while meeting constraints.

DETAILED DESCRIPTION OF THE DRAWINGS

Figure 1:
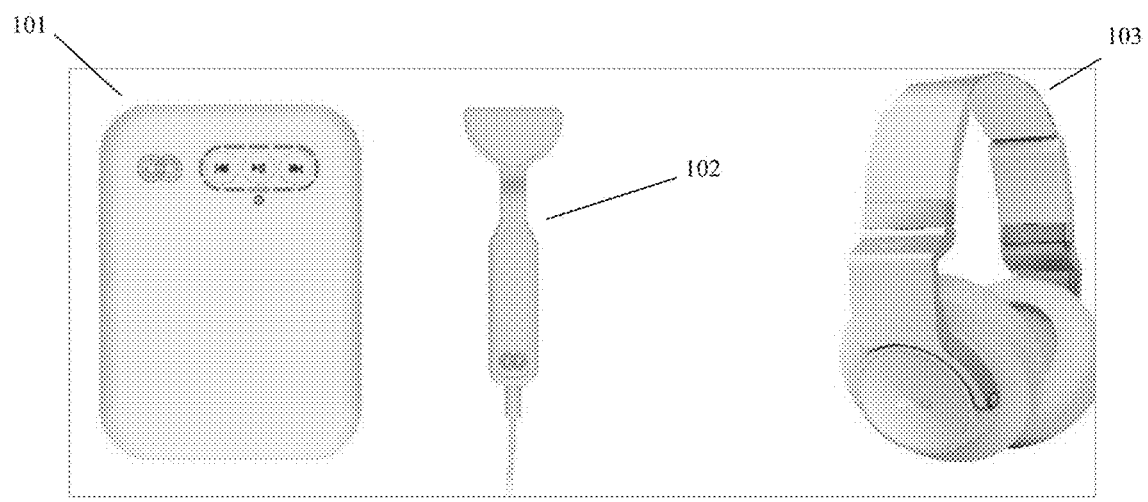
FIG. 1 is a system in accordance with the present invention.

The aspects of the technology mentioned above, as well as additional aspects, will now be described in greater detail. The aspects may be used individually, all together or in any combination of two or more, as the technology is not limited in this respect. The present invention combines auditory and somatosensory bimodal stimulation to improve the symptoms of a neurological disorder of the auditory system. Neurological disorders of the auditory system include for example tinnitus, hyperacusis, misophonia or phonophobia. For convenience only, tinnitus is referred to in the examples below, however it will be appreciated that the systems described may be extended to any of the disorders. A sample system in accordance with the invention and as shown in FIG. 1, including a stimulus generation unit 101 or controller and a somatosensory stimulation unit 102. The controller receives an audio signal as an input and generates a plurality of actuation signals representative of the audio signal. This plurality of actuation signals are delivered to the somatosensory stimulation unit 102. Controller 101 also generates a corresponding binaural modified audio signal for delivery to a subject being treated. Delivery of the modified audio signal is carried out using headphones or audio transducers 103 as shown in FIG. 1. While shown as part of the system in FIG. 1, this is as an example only and the system may be supplied without the headphones. While these headphones are shown as over the ear headphones it will be appreciated that any other audio delivery mechanism may be used for example loudspeakers located proximal to the patient, bone conduction transducers, cochlear implants, in ear audio transducers such as in-ear headphones or hearing aids, sound-from-ultrasound technology or over-ear audio transducers. The headphones shown in FIG. 1, in an embodiment, are arranged to deliver stereo audio having a −3 dB frequency response of 20 Hz to 20 kHz, and a dynamic range of >90 dB. The auditory and somatosensory stimulation are delivered substantially simultaneously to a patient. This simultaneous delivery introduces a fixed delay between audio and somatosensory (up to +1-50 ms). Alternatively a random variation in delay between audio and somatosensory stimuli (up to +1-50 ms) with a rectangular probability density function, or up to a standard deviation of 20 ms for a Gaussian probability density function) may be introduced to cover a wide range of latencies over the course of a treatment session.

Somatosensory Stimulation Unit.

The somatosensory stimulation unit in a preferred embodiment is an intra oral device (IOD). The IOD of FIG. 1 is dimensioned to be located on the tip (dorsal anterior region) of the tongue of the subject undergoing treatment. It will be appreciated however, that the device may also be dimensioned to be located on any part of the subject wherein a relevant nerve for the treatment of the neurological disorder can be stimulated, for example Transcutaneous, for example on the,
  i. Cheek (maxillary branch of trigeminal nerve)
  ii. Jaw (mandibular branch of trigeminal nerve)
  iii. Forehead (ophthalmic branch of trigeminal nerve)
  iv. Neck (sub-mandibular branch of trigeminal nerve)
  v. Ear/Pinna (vagus nerve)
  vi. Lips (mandibular branch of trigeminal nerve)
  vii. Shoulders and Neck (Accessory Nerve, cervical spine nerves C1 and C2)

Trans-mucosal
  i. Dorsal-anterior region of the tongue (lingual mandibular branch of trigeminal nerve)
  ii. Ventral-anterior region of the tongue (hypoglossal nerve)
  iii. Gums (maxillary branch of trigeminal nerve)

Non-contact, however, this applies to an Electro-magnetic stimulation only (for example, e.g. Repetitive Transcranial Magnetic Stimulation, (rTMS))
  As above (both trans-cutaneous and trans-mucosal sites) OR
  Trigeminal nuclei
  Cochlear nuclei
  Auditory cortex Implantable
  As above (both trans-cutaneous and trans-mucosal sites) OR
  Cochlear/auditory nerve
  Cochlear nuclei
  Trigeminal nuclei
  Auditory cortex
  Vagus nerve In the embodiment shown in FIG. 1, the somatosensory stimulation unit is an intra oral device (IOD). The configuration shown in FIG. 1 relates to a first embodiment wherein the stimulus generation unit is located remote from the IOD at the control unit 101. In the examples below, this configuration is referred to as MB1. In an alternative configuration, referred to as MB2, the stimulus generation unit may be located local to the IOD 102, for example using a microcontroller or other programmable device to generate the stimuli.

Figure 2:
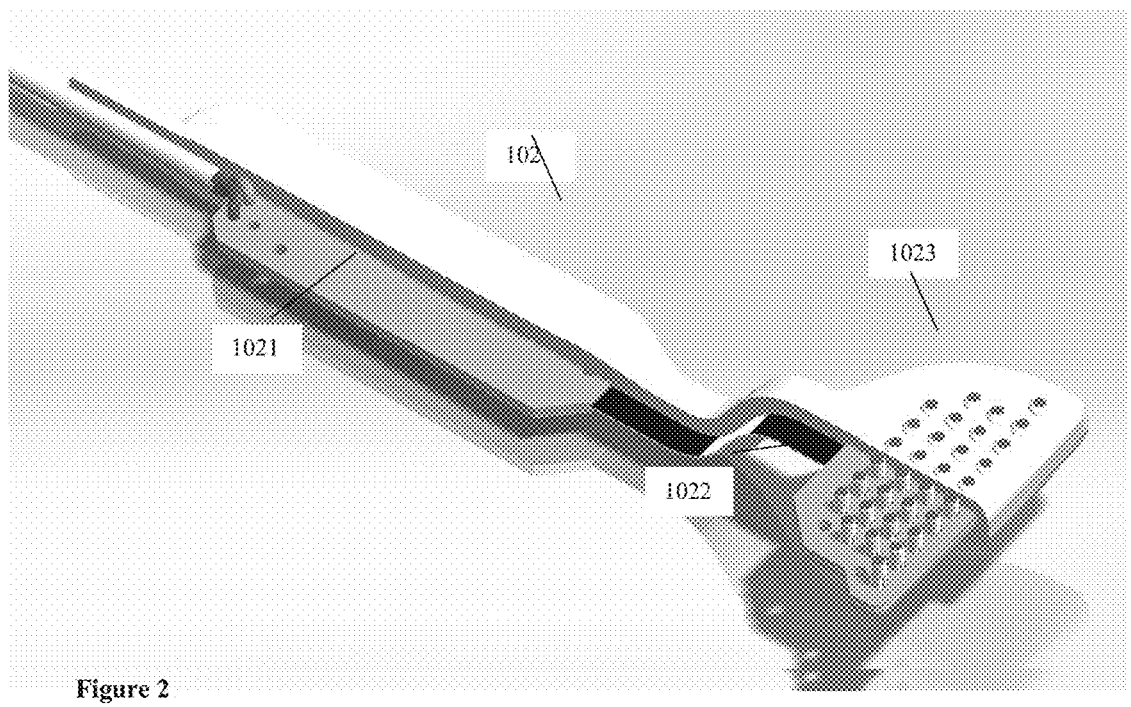
FIG. 2 is an intra-oral device in accordance with an aspect of the present invention

The IOD or somatosensory stimulation unit includes an array of stimulators 1022 each of which can be independently actuated to apply a somatosensory stimulation to a subject synchronously with the modified audio signal. In the MB1 configuration where the IOD is controlled by the controller 101 it will be appreciated that a comparator is required for each stimulator in the array in order to drive each stimulator or electrode. These comparators may be located on the circuit board in the controller 101. In the MB2 configuration, the microcontroller is configurable to drive the electrodes or stimulators directly, said microcontroller and support components may be located on printed circuit board 1021. This configuration minimises the component count and thus the cost. The PCB 1021 and the array 1022 as shown in FIG. 2 are encapsulated within a moulded unit 1023. In an embodiment, the moulded unit is over moulded. Such a moulding process is suitable for an injection moulding process, thus minimising the cost of the IOD. It will be appreciated that to seal the IOD, a Parylene C coating for example may be applied to the PCB before over moulding to seal it. Parylene is a hydrophobic polymer microfilm applied by Chemical Vapour deposition. Parylene dimers are vaporised and converted to a monomer at 690° C. It is then introduced to a vacuum chamber where it forms a polymer coating at room temperature. Applying a Parylene C layer of 12-15 μm seals the IOD and mitigates the risks associated with saliva ingression to the PCBA, leaching toxins, egressing back out, and being ingested by the subject.

Figure 3:
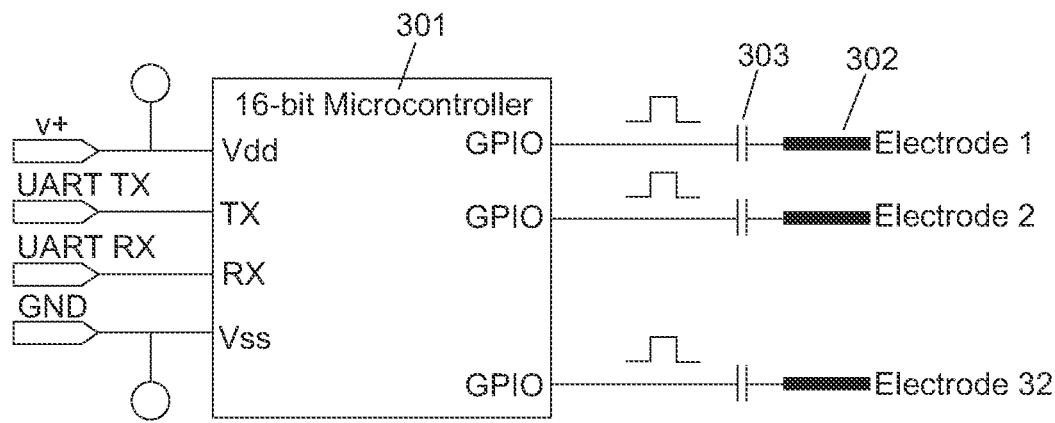
FIG. 3 is a microcontroller configuration in accordance with an embodiment of the present invention.

To generate a strong percept or sensation using the IOD array stimulation in the MB2 configuration, a peak driving voltage of at least 5V may be required. An exemplary microcontroller arrangement is shown in FIG. 3. The microcontroller 301 is a 16 bit microcontroller, however, it may also be an 8 bit or 32 bit microcontroller, an FPGA, custom chip or the like. The microcontroller includes a plurality of inputs and a plurality of outputs 302 arranged to drive each individual electrode in the stimulator array. Each line driving the electrodes has a capacitive element 303 thereon to prevent direct currents from flowing through the subject.

In the MB1 configuration the power supply provided to the voltage input of the IOD is provided by the controller or stimulus generation unit remote from the array. In the alternative MB2 configuration if the IOD is powered by the controller, no additional regulation circuitry is required within the IOD itself and accordingly, the component cost and requirement for the IOD is reduced. A local decoupling capacitance (not shown) may be provided on the MCU supply rail to supply worst cast transients due to electrode drive switching. In the configuration proposed, the MCU 301 drives each electrode by way of the series capacitor 303 on the drive line from the GPIO to the electrode. This configuration facilitates a subset of electrodes to be active at any given instance in time, thereby allowing all other electrodes to act as a stimulus current return path.

The IOD may be detachable from the controller or may be integral thereto. A Universal Serial Bus, USB, optionally with custom overmoulding, or other connector may be provided for connecting to the controller. This other connector may prevent connection to non-medical equipment. The top surface of the electrode array within the encapsulation 1023 that makes contact with the mucosal membrane is masked so an electrode-membrane interface is unaffected by the coating process. It will be appreciated that the masking material must be bio-compatible. Parylene C as described above is chemically inert and biocompatible.

While described herein as intraoral, it will be appreciated that a suitable array may comprise two or more arrays. These arrays can be contained in separate devices and for example may be located across the back of the neck, or split between one side of the face (jaw) and the opposing side of the face. In an additional embodiment, the somatosensory stimulation unit also comprises a second array comprising at least two stimulators (not shown in the figures). These stimulators are in an arrangement, arranged relative to the array of stimulators and configured to deliver a pseudo stimulus to the subject. This pseudo-stimulus includes additional stimulus channels which are configurable to provide a sensation of an effect to the patient but which are not part of the therapeutic stimulus. The purpose of these is in cases where the main stimulus delivered by the first array is not perceptible, or weakly perceptible. The pseudo stimulus can be activated to improve or increase the sensation perceived by the patient. Further, this facility assists in clinical trials where a "fake" treatment is required. This pseudo stimulus may be implemented with a single stimulus or two stimuli channels, however any number of stimuli channels may be facilitated. In a configuration the pseudo stimulus is asynchronous to any auditory stimulus. Further it may have a low duty cycle relative to the therapeutic stimulus. Furthermore, the pseudo stimulus may be blocking in nature.

In an alternative embodiment, said pseudo stimulus can be elicited through the IOD 102 without any additional stimulators. This is achieved by multiplexing in time the pseudo stimulus with the treatment stimulus. In this scenario a mark:space ratio of at most 10% would be required to impart significant stimulus percept to the subject, while delivering the treatment stimulus for at least 90% of the treatment session duration. The main constraints in the design of a suitable audio signal for auditory stimulation of a subject are as laid out in table 1 below.

In a first example (MB1), two audio tracks were chosen, namely "Forest Raindrops" by Relax With Nature as the foreground, broadband sound and Erik Satie, "Gnossiennes" and "Gymnopodies" performed by Reinbert de Leeuw. The mixing was performed as follows: Both audio tracks are extracted to 16 bit 44.1 kHz way files and normalised to −0.1 dB. Waves L3 compressor may be used on both, with a threshold setting of −12 dB, no dither, other settings default. The amplitude of the Satie was reduced by 18 dB, extra reverb applied (to enhance the illusion of the music coming from the distance) and was then mixed with the Forest Raindrops with an overall gain of −1 dB to avoid saturation during the mixing. The resulting mix was truncated to 30 minutes, and a short lead in crescendo and lead out decrescendo, before being exported as a 16 bit 44.1 kHz .wav file. In an alternative example (MB2) the two sound tracks chosen included "Forest Raindrops" by Relax With Nature as the foreground, broadband sound and Erik Satie, "Gnossiennes" and "Gymnopodies" performed by Therese Fahy (the applicant commissioned Therese Fahy to perform these works, which were recorded in RTE Radio Studio 1 on the 7$^{th}$ and 8 Jan. 2015, on a Steinway Grand piano). The mixing was performed as follows: Both audio tracks were extracted to 16 bit 44.1 kHz way files and normalised to −1 dB (to pre-compensate for the overall gain reduction of −1 dB applied in the first configuration's audio mixing). Waves L3 compressor was used on both, with a threshold setting of −12 dB, no dither, other settings default.

TABLE 1

| Audio stimulation design constraint | Rationale |
| --- | --- |
| The audio stimulus should be spectrally broad | To stimulate as many of the afflicted auditory pathways as possible |
| The audio stimulus should contain a high density of fine-grained temporal sounds | So that the auditory processing structures can make frequent correlations between the sound and the electro-tactile stimulation (ETS). |
| The fine-grained sounds within the audio stimulus should be randomly spread in the temporal and spectral domains, | This will ensure that the spatial and temporal characteristics of the somatosensory stimulation (derived from the audio) will be also random, thereby facilitating a neuromodulation-only mode of action. |
| The audio stimulus should promote a sense of relaxation in patients | To maximise patient's comfort To reduce patient's stress levels To maximise patient's tolerance of the treatment |

TABLE 1-continued

| Audio stimulation design constraint | Rationale |
|---|---|
| The audio stimulus should eliminate repetition within the period of a standard treatment session (30 minutes) | To minimize boredom, thereby increasing the patient's tolerance of the treatment To increase patient's attentiveness during the treatment |
| The audio stimulus should have limited dynamic range, limited close to what the dynamic range of ETS perception on the tongue is. | So that the mapping to the ETS pattern results in a relatively consistent stimulus intensity. To maximise the periods during which the affected auditory structures are stimulated, especially in patients that have significant hearing loss in certain bands. There is no basis to believe that wide dynamic range would have any additional benefit to the patient. |
| The audio stimulus should contain a musical sound track mixed with the broad band foreground, such that it sounds to the patient that the source of the music is originating from a spatial location that is far away. For example, the broadband noise may include a mixture of speech. | To increase patient's attentiveness during the treatment, thereby helping to promote neuroplasticity To help promote relaxation in the patient |
| The audio stimulus should be filtered to compensate for their hearing loss, or band-boost filtered at a frequency that is close to the patient's hearing profile roll-off frequency, or to their tinnitus match frequency if their hearing is normal | To boost the stimulus, and resulting neuromodulation in the region of the patient's hearing deficit, or at a frequency that most closely matches their tinnitus dominant frequency. |
| The audio stimulus should be stereo | To maximise patient's comfort by simulating a sense of space (mono audio through headphones can make the sound appear as though it emanates from a single, central point) To facilitate adequate auditory stimulation for patients that have an asymmetrical hearing loss or tinnitus loudness. |

Four versions of the sound track were created:
With the Satie mixed at an amplitude of −12 dB
With the Satie mixed at an amplitude of −15 dB
With the Satie mixed at an amplitude of −18 dB
With no musical component in the mix The resulting mixes were truncated to 31.5 minutes, and a short lead in crescendo and lead out decrescendo, before being exported as a 16 bit 44.1 kHz .wav files.

The files above are examples only and it will be appreciated that other combinations of audio stimuli could also be implemented as long as they meet the design criteria set out above. The system as described above may also have the facility to select one of a multiple of files. These files may be selectable by the subject.

Following the determination of the audio input, an additional audio stimulus filtering is implemented. Most tinnitus patients suffer from a hearing loss at one or more frequencies, with the tinnitus most commonly associated with the side ipsilateral to their hearing loss. In order to ensure there was additional auditory stimulation in the frequency bands of highest hearing loss and/or their tinnitus match frequency, a boost filter is implemented to facilitate compensation for the relevant frequency bands.

The constraints of the filtering include:
To have the centre frequency configurable by the clinician when the device is being fitted to the patient, where the set of available configuration frequencies is also covered by a standard high-frequency audiometer (250, 500, 750, 1000, 1500, 2000, 3000, 4000, 6000, 8000, 10000, 12500 Hz etc.)
To boost the gain of the audio by 12 dB at the centre frequency (so that a standard bi-quad filter implementation could be used)
To have a fixed boost bandwidth (in proportion to the centre frequency), of half the centre frequency.

Accordingly a set of filters is configurable. To meet the set of constraints above the filters are configurable as follows (this example represents the MB2 configuration) in Table 2. The audio stimulus filtering in the MB1 configuration is the same, except the 10 kHz and 12.5 kHz bands were not utilised, because at the time only a standard audiometer was used (audiological assessments conducted up to and including 8 kHz). The filters are examples only, and in this case designed for ease of implementation and low processing power to implement. These filters spectrally modify the audio input to compensate for a deficit in the hearing profile. For example applying a band boost filter with centre frequency correlated to fall-off frequency as determined by the patient's audiogram will compensate for the deficit. A band boost filter may be calibrated in accordance with the steepest roll off of the audiogram of the patient with the half power bandwidth of the band boost filter between 0.5 and 1.5 octaves normalised to the centre frequency, and with a boost magnitude of at least 12 dB.

TABLE 2

| Filter Number | Centre Frequency [Hz] +/− 2% | −3 dB Bandwidth [Hz] | Boost Ratio |
|---|---|---|---|
| 1 | 250 | 125 | +12 dB |
| 2 | 500 | 250 | +12 dB |
| 3 | 750 | 375 | +12 dB |
| 4 | 1000 | 500 | +12 dB |
| 5 | 1500 | 750 | +12 dB |
| 6 | 2000 | 1000 | +12 dB |
| 7 | 3000 | 1500 | +12 dB |
| 8 | 4000 | 2000 | +12 dB |
| 9 | 6000 | 3000 | +12 dB |
| 10 | 8000 | 4000 | +12 dB |
| 11 | 10,000 | 5000 | +12 dB |
| 12 | 12,500 | 6250 | +12 dB |

Alternatively, the filter may be a boost filter calibrated based on the inverse of the audiogram of the subject in the ipsilateral ear and the filter may be configured to compensate for deficits of at least 30 dB and operable in the range 500 Hz to 16 kHz. It will be appreciated that other filter implementations can be implemented that are better at compensating for the subject's hearing loss.

Method of Auditory Stimulation

It will be appreciated that the use of high-fidelity over-ear headphones coupled with the necessary signal processing is a suitable method of auditory stimulus delivery in accordance with the present invention, because of the widespread tolerance by the users/patients to them and the high degree of comfort they afford to the patient. In particular situations, it may be preferable to use other transducers, including hearing aids, proximal loudspeakers, and cochlear implants. For example, if the patient has a middle ear disease or other condition that results in a significant conductive hearing loss, a bone conduction transducer may be an acceptable alternative. In this situation, the inner ear mechanisms (including the cochlear function) may be relatively unaffected, and so auditory stimulation via bone conduction transducers would enable such patients to benefit from the treatment. In an alternative scenario, for example, wireless headphones are unsuitable where the patient suffers from electromagnetic hypersensitivity (EHS), proximal loudspeakers or wired headphones may be used. Sufferers of electromagnetic hypersensitivity (EHS) tend to be particularly affected by the knowledge that they are in close proximity to RF sources. In an alternative scenario, for example where the patient has difficulty finding a location that is suitably quiet, in-ear sound-isolating earphones such as Shure SE215 or over ear noise cancelling headphones may be used. It will be appreciated that some patients are significantly affected by tinnitus levels that are less that 10 dB HL, and where there is the requirement that their tinnitus is not over masked during treatment, the background noise levels may need to be 20 dBA or less. Many patients live in environments that have consistent noise levels well above this level. In an alternative scenario, for example, where the patient has profound SNHL in ears that are also affected by tinnitus, cochlear implants may provide an alternative. This is noted where the hearing loss is sensorineural and profound, such as in cases of congenital deafness, acoustic or vibration transducers may provide no stimulus to the auditory pathways. In such cases, cochlear implants may provide the only means of stimulation the auditory branch of the VIII nerve. In an alternative, where the patient has a phobia of wearing headphones, or the patient has a dermatological condition that prevents the use of contact devices around the ear or head, proximal loudspeakers may be used.

Of the many methods of delivering somatosensory stimulation to the V cranial (trigeminal) nerve, electrical stimulation (commonly referred to as electro-tactile stimulation, ETS) is implemented in accordance with the present invention for the following reasons:

It is highly versatile

A high degree of control of the nerve depolarisations is possible, by controlling the timing, amplitude, topography and delivery mode (voltage vs current mode) of the electrical stimulus.

Devices that transduce somatosensory stimulation electrically can be manufactured cost effectively (as compared with electro-mechanical methods of transduction for example) Other methods of somatosensory stimulation can also be used, for example Vibration transduction (e.g. via an array of vibrating pins)

Force transduction (e.g. via an array of force controlled pins, akin to an electronic Braille display)

Such methods can be used to in situations where electrical stimulation is not feasible, for example During research investigations where the effects of stimulation need to be evaluated simultaneous to fMRI.

In situations where it cannot be ascertained if the level of electrical stimulation is too high (over stimulation), or too low (sub-threshold stimulation). This is especially pertinent if the mechanism of action (MOA) is primarily at sub-cortical levels, where the optimum level of electrical stimulus may in fact be lower than that which is perceptible (since perception occurs at the cortical level). It is also pertinent where the frequency of the electrical stimulus is so high that it keeps the target nerve fibres in a constant state of depolarisation (yet still elicits a percept due to the paraesthesia effect), or where the amplitude of the electrical stimulus is so high that the field intensity under electrodes adjacent to the active electrode that non-targeted nerve fibres are being depolarised. Mechanical stimulation can be easily set to a level that is neither too high, nor too low, as the qualitative level of perception the patient reports will be commensurate with the degree of nerve impulses passing through the sub-cortical structures.

In accordance with the embodiments of the present invention, the somatosensory stimulation is applied to the anterio-dorsal surface of the tongue. It will be appreciated that the tongue is a mucosal surface that is coated with a replenishing electrolyte (saliva) that enhances transcutaneous electrical stimulation. Furthermore, the anterio-dorsal surface of the tongue possesses one of the highest somatic nerve densities in the human body and as a result has a disproportionately large representation in the somatosensory homunculus. Unlike with many currently existing neuromodulation technologies for treating neurological conditions (e.g. vagus nerve stimulation for the treatment of Tinnitus, (De Ridder, Dirk, et al. "Safety and efficacy of vagus nerve stimulation paired with tones for the treatment of tinnitus: a case series." *Neuromodulation: Technology at the Neural Interface* 17.2 (2014): 170-179), the tongue can be stimulated without any surgical intervention.

The lingual branch of the trigeminal nerve innervates the anterior surface of the tongue. Studies have demonstrated that there are important anatomical and functional links between the trigeminal nerve and central auditory structures, such as the cochlear nuclei. However while described herein with reference to the anterio-dorsal surface of the tongue, other sites of stimulation could be used, in particular sites that allow transcutaneous stimulation of various branches of the trigeminal nerve, Vagus nerve, or C1/C2 nerves. One of the key parameters with respect to implementing bi-modal neuromodulation systems is that of the signal bandwidth represented. For example, the information rate of the auditory stimulus can be set very high, since the human hearing apparatus is capable of decoding very complex sounds.

Perceptual encoding of complex auditory signals can only achieve high fidelity with 64 kbits/s or higher for 16 bit dynamic range, 12 kHz bandwidth (24.050 kHz sample rate and covering a 8 octave range from about 50 Hz to 12 kHz), even when utilising the most advanced perceptual encoding algorithms (e.g. AAC, Vorbis/OGG).

As will be described later, the perceptual encoding dynamic range for amplitude via electro-stimulation on the tongue is approximately 9 levels including zero (which can be represented digitally with 4 bits of information), and the frequency range of operation limited to between 500 Hz and 8 kHz (a range that spans 4 octaves).

Therefore, a minimum 8 kBits/s (==64 kBits*(4/16)bits* (4/8) octaves) of equivalent information would need to be encoded into the somatosensory domain for high-information stimulation.

Audio to Somatosensory Mapping

Figure 17:
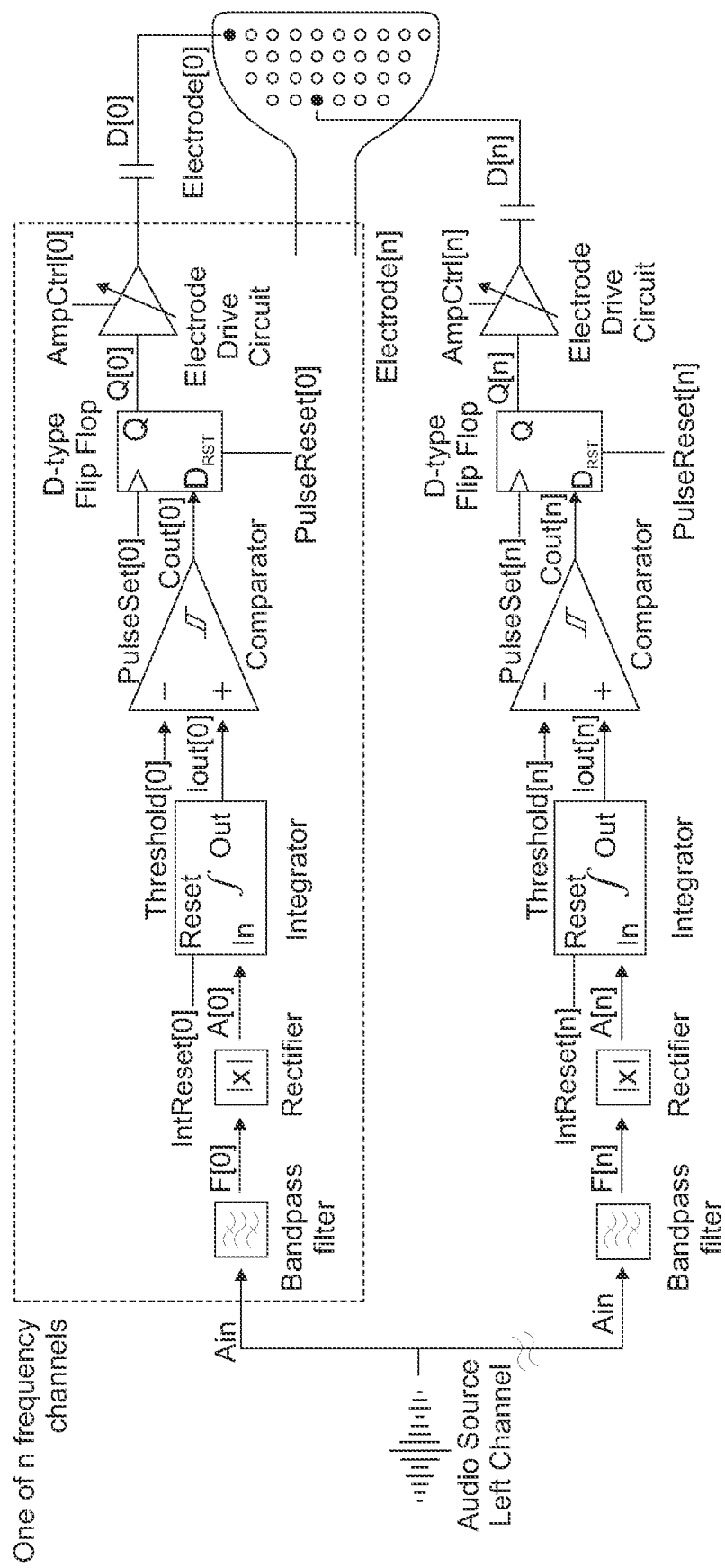
FIG. 17 is a schematic of an alternative audio to somatosensory mapping
Figure 18:
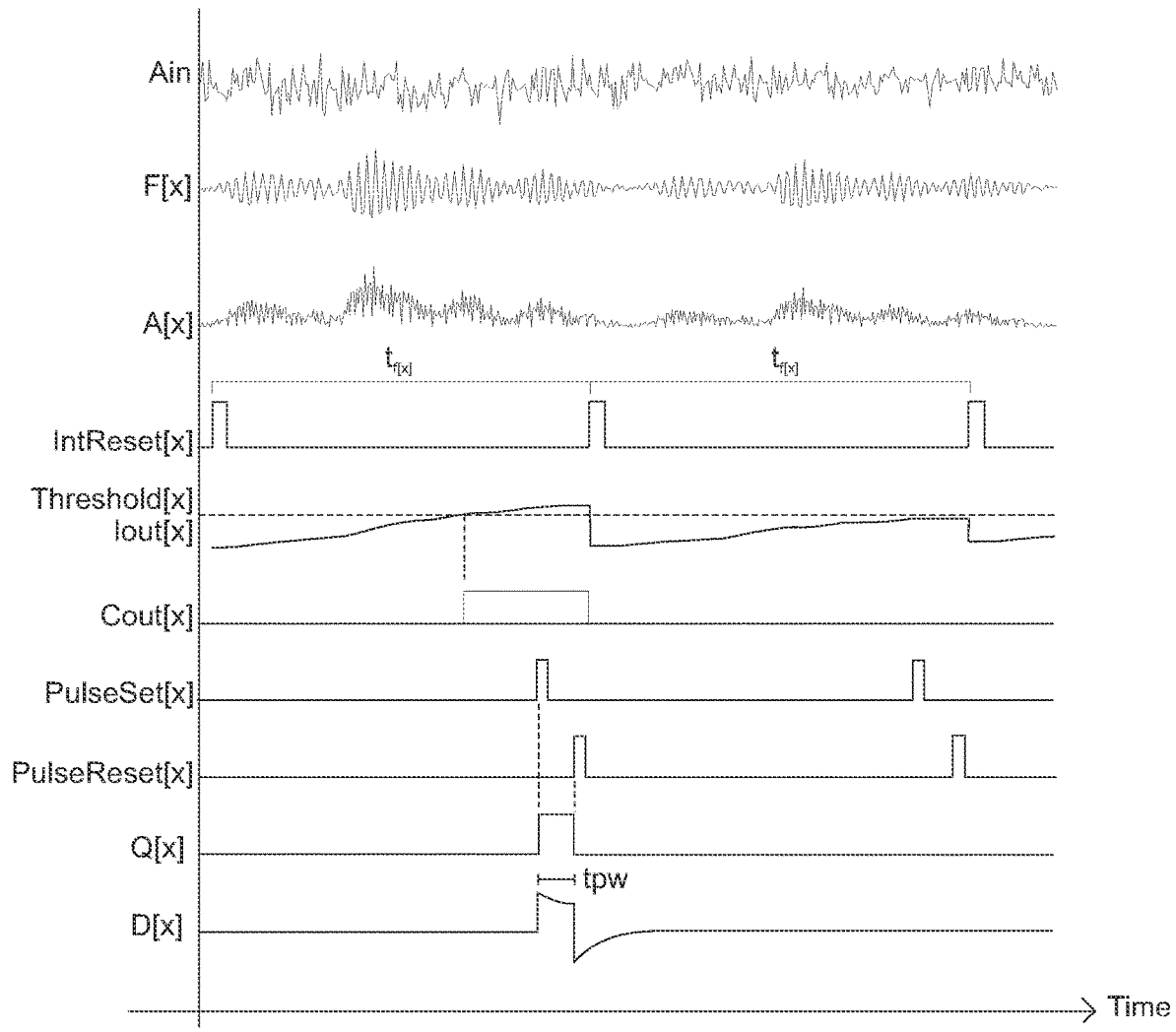
FIG. 18 is a timing diagram of alternative audio to somatosensory mapping

Several types of mapping between the audio and somatosensory stimulus are possible, some of which are described in the table 3 and as shown in FIGS. 17 and 18.

The MB1 and MB2 use spectral transformations with high temporal and low frequency resolution, because of the limited frequency resolution required (critical bands according to the Bark scale, see below) and the resulting efficiency of implementation.

It will be appreciated that both temporal and spectral mapping of the audio to somatosensory stimulation maximises the probability of high efficacy.

Spectral Mapping

The spectral information can be mapped to somatosensory information in several ways, including:
- Pulse position coding of the ETS signals
- Pulse amplitude coding of the ETS signals
- Tonotopical mapping—one electrode assigned to each frequency region The MB1 and MB2 use a tonotopical mapping, akin to that which occurs in the cochlea (where differing frequencies cause a tonotopic spread of hair cell stimulation). In this regard, the auditory stimulus is analysed as a discrete number of frequency bins, and each frequency bin is assigned to one of a multitude of electrodes in the array, covering the range of frequencies that are typically affected in age related and noise induced hearing loss (as research shows that in most cases subjective tonal tinnitus occurs in a frequency band close to the dip frequency (noise induced hearing loss) or roll-off frequency (for age-related or ototoxicity related sensorineural hearing loss) of the patient.

Spatial Arrangement of Electrodes

Two separate spatial arrangements of the electrodes are considered, each with advantages over the other as outlined in Table 4. For the MB1, as used in the clinical investigations in 2012, the single array approach is used. The single array approach is also useable for the MB2 configuration, however the MB2 can also be configured to utilise the split-array configuration.

TABLE 3

| Mapping Type | Temporal Resolution | Frequency Resolution | Description | Example |
|---|---|---|---|---|
| Threshold Detection | Very High | None | Mapping specific temporal events in the audio stimulus to somatosensory events, with no consideration of spectral information, Note: This mapping is amenable to a single electrode (monaural) or dual electrode (split array) arrangement. | Analysing the energy of the auditory signal over temporally short periods and triggering somatosensory events based on the magnitude of the energy within each period. |
| Spectral | Low | High | Mapping spectral information directly to somatosensory events, with significant blurring of the temporal information | Analysing the spectral content of the auditory stimulus over temporally long periods, and triggering somatosensory events based on threshold detection of energy at particular frequencies. |
| Spectral | High | Low | Mapping spectral information directly to somatosensory events, while maintaining temporal resolution but limited frequency resolution | Dividing the auditory stimulus into short analysis frames, and estimating the spectral content within each frame and triggering somatosensory events based on threshold detection of energy at particular frequencies within each analysis frame. |
| Spectral | High | High | Mapping spectral information directly to somatosensory events, while maintaining temporal resolution and frequency resolution | Dividing the auditory stimulus into variable length overlapping analysis frames, and estimating the spectral content within each frame (similar to performing a wavelet transform) and triggering somatosensory events based on threshold detection of energy at particular frequencies within each analysis frame. This mapping is covered in an alternative configuration. |

TABLE 4

|  | Single array | Split array |
| --- | --- | --- |
| Mechanism of Action (MOA): | Primarily cortical levels | Cortical and sub-cortical levels |
| Advantages: | Electrodes can be used to represent twice as many frequency bands The issue of centring the array is not as critical as in the case for the split array because the in the latter case it is required that the stimulation operates on the ipsilateral side only | May be more effective at promoting neuroplastic changes in sub-cortical structures, because the auditory stimulus for each side is matched to the ipsilateral somatosensory somatosensory stimulus |
| Disadvantages: | May not be as effective at promoting neuroplasticity in sub-cortical structures, because there will be a mismatch between the auditory stimulus and the somatosensory stimulus on the ipsilateral side. | Only half as many frequency bands can be presented with a given number of electrodes Centring the array, such that stimuli affect the ipsilateral side only, poses design challenges in certain embodiments (such as tongue stimulation) |

Somatosensory Stimulation—Spectral Encoding

Given that there is a finite number of electrodes possible in the hardware design, the spectral encoding is such that each electrode maps to a particular frequency bin. The choice of an appropriate division and range that these frequency bins cover is of critical importance to the design of the system.

Four possible choices for the spacing of the frequency bins are considered:
 Linear
 Logarithmic (base2)
 Perceptual (such as a Mel scale)
 Bark scale (based on critical bands)

Linear Spectral Encoding

Spectral encoding using linear scale is not optimal because no part of the human auditory system, either in pitch or amplitude, operates on a linear scale (our perception of both pitch and loudness are both on logarithmic scales). A linear scale is very inefficient at representing pitches that extend across such a significant range of our hearing, and as a result would result in highly disproportionate weighting to the higher frequencies in our hearing range than the lower frequencies.

Logarithmic (Base2) Spectral Encoding

A logarithmic (base2) scale is more suitable than a linear scale, especially where the audio stimulus comprises of harmonic music. However, it does not match the physiology of the cochlea very well (as per the Place theory), especially at higher frequencies (where perceptual scales are more appropriate). One advantage however is that chords or harmonics in any musical components would align with patterns of electrodes, whereas with the perceptual scale (such as Mel or Bark scale) only dissonant chords would align with patterns of electrodes.

Perceptual (Mel Scale) Spectral Encoding

One of the most popular perceptual scales to represent the human frequency range is the Mel scale (a scale where pitches are perceptually equidistant from each other) (Stevens, Stanley S. "On the psychophysical law." *Psychological review* 64.3 (1957): 153; Stevens, Stanley S., and John Volkmann. "The relation of pitch to frequency: A revised scale." *The American Journal of Psychology* (1940): 329-353). It is based on psychoacoustic experiments on humans, where the resulting steps in the scale are judged equidistant in pitch. It is not linear with respect to log (base2) scale, and as such, the harmonics within simplex or complex tones will not align with frequency bins that are spaced according to the Mel scale, especially at the higher frequencies.

Bark Scale (Psychoacoustic Critical Bands)

A less popular perceptual scale to represent the human frequency range is the Bark scale (a scale where pitches are perceptually equidistant from each other) (Zwicker, Eberhard. "Subdivision of the audible frequency range into critical bands (Frequenzgruppen)." *The Journal of the Acoustical Society of America* 33 (2) (1961): 248). Like the Mel scale, it is based on psychoacoustic experiments on humans, where the resulting steps in the scale are judged equidistant in pitch. However, unlike the Mel scale, it is divided neatly into the critical bands of human hearing (the critical band is the band of audio frequencies within which a second tone will interfere with the perception of the first tone by auditory masking).

In accordance with the embodiments described herein, the MB1 and MB2 embodiments base frequency binning on the Bark scale critical bands when there are limited electrodes available (as in the split array design), and a log (base2) scale when there is less of a limitation on the number of electrodes (as in the single array design).

Somatosensory Stimulus Spectral Bin Limits

In order to make the most efficient use of available resources (in terms of the complexity of the system, the number of available electrodes etc.), the range, or limits, over which the frequency bins are spread required consideration.

Starting at the top frequency, when testing is carried out above 8 kHz, cases of individuals with tinnitus without hearing loss are quite rare (Salvi, R. J., Lobarinas, E. & Sun, W., (2009), "Pharmacological Treatments for Tinnitus: New and Old", Drugs of the Future, 34, 381-400). Accordingly, for both the MB1 and MB2 configurations the upper bound was limited to 8 kHz. The lower frequency was chosen as the 1 percentile corner frequency of the population that suffer from sensorineural hearing loss (Congenital, NIHL, presbycusis, ototoxic induced hearing loss etc.), which is approximately 500 Hz (Congenital cytomegalovirus (CMV) infection & hearing deficit (Fowler, Boppana) 2005, Fowler; CMV A Major Cause of Hearing Loss in Children (2008), http://www.cdc.gov/nchs/data/series/sr_11/sr11_011acc.pdf (page 7, FIG. 5)).

Arrangement of the Frequency Bins

For a split-array stimulator (split down the medial line of the tongue), and in accordance with the embodiments described herein a minimum of 16×2 electrodes is required (32 electrodes). With the constraints above (covering all critical bands in the range 500 Hz to 8 kHz), the following frequency bins are required (as per the bark scale) [Hz]:
570 700 840 1000 1170 1370 1600 1850 2150 2500 2900 3400 4000 4800 5800 7000

Figure 4:
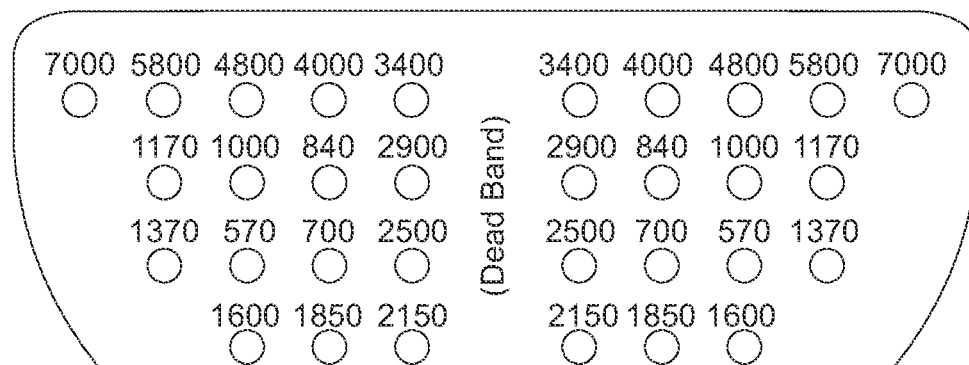
FIG. 4 is a sample layout of a split array in accordance with the present invention.

An electrode array of size 32 electrodes was chosen for the MB1 design to be able to accommodate the split-array design. A deadband may be included between the right side and the left side stimulators. This is illustrated in FIG. 4.

The dorsal anterior region of the tongue, where spatial resolution and sensitivity are at their highest, can easily accommodate the 32 electrodes on a grid spacing of 2 mm.

For a single array design, in order to make use of all 32 electrodes, the frequency bin spacing is decreased such that there are 8 bands per octave, thereby dividing the required frequency range into 32 logarithmically evenly-spaced bands across the full frequency range of interest (500 Hz to 8 kHz). Frequency bins are separable equidistant on a log (base 2) scale to maintain a consonant harmonic relationship between the frequency bins. Within these constraints (8 kHz top frequency, and 8 bins per octave, and approximately 500 Hz for the lowest frequency bin), the following frequency bins are required [Hz]:

---
545 595 648 707 771 841 917 1000 1091 1189 1297 1414 1542 1682 1834 2000 2181 2378 2594 2828 3084 3364 3668 4000 4362 4757 5187 5657 6169 6727 7336 8000
---

Figure 5:
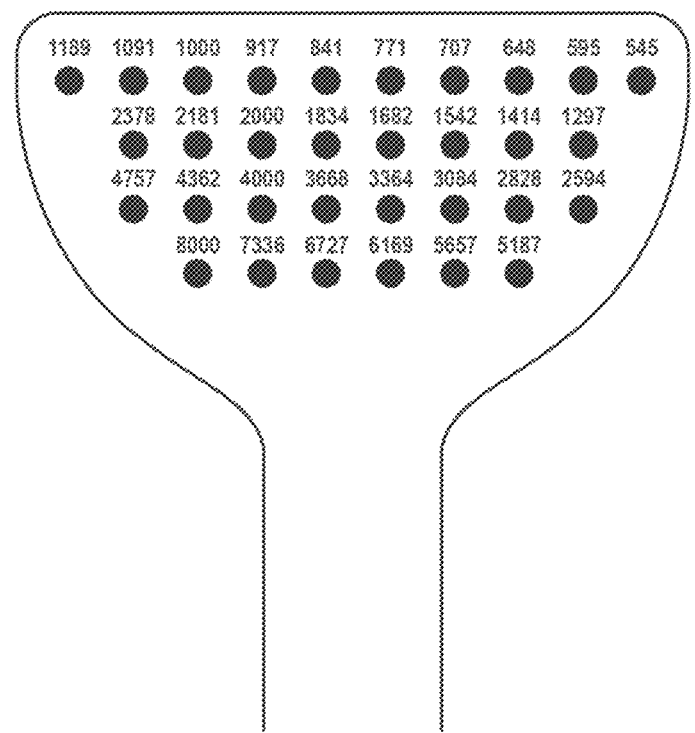
FIG. 5 is a sample layout of a single array in accordance with the present invention.

These frequencies are mapped as shown in FIG. 5 (viewed from the electrode side of the IOD) and are both suitable mappings used in both MB1 and MB2 configurations. As shown the frequencies that are most typically affected in patients with hearing loss related tinnitus (the highest frequencies) are situated on the two bottom rows—this corresponds to the region that is closest to the tip of the tongue and as such is the area of highest somatosensory nerve fibre innervation density.

An alternative arrangement in which the bins are arranged spirally could be used in an alternative embodiment of the device as illustrated in FIG. 4.

Neuromodulation, Perception and Paraesthesia.

Somatosensory stimulation may be a trans-mucosal or trans-cutaneous electro-tactile stimulus (ETS). From a neuromodulation point of view, and where the mechanism of action (MOA) is based in sub-cortical regions of the brain, the act of depolarizing somatosensory nerve fibres may be sufficient for the device to be effective, since the depolarising of the nerve fibres should result in neural spikes reaching one or more of the subcortical structures in the brain. However, depolarising somatosensory nerve fibres is not always sufficient to illicit a percept and therefore it cannot be assumed that a percept is essential for the stimulation to be effective.

On the other hand, where the MOA is primarily at the cortical levels (e.g. from a perceptual perspective), then it is almost certainly essential that the patient perceives the stimulus for the treatment to be effective.

Even if the MOA is only at sub-cortical levels, it will be appreciated that it is important that the patient can perceive the stimulation for example, so that the patient is aware that the device is operational. If there is no percept, the patient is less likely to comply with the treatment. Feedback from patients that participated in the 2012 trial (using the MB1 device) revealed that a strong percept was important so that they could 'feel the treatment working'. In a further example, the feedback is important to ensure that the electrodes are making the necessary contact with the patient's tongue. Patient feedback about the perceived strength and location of the stimulus is the only way to know that the electrodes are positioned correctly and hence the only way to ensure compliance with the treatment regime. In a further example, this feedback is used to enhance the placebo effect. Even though the placebo effect is not the principle mechanism of action of the device, it is likely to enhance the device's effectiveness for some patients.

The two principle mechanisms of perception from electro-tactile stimulation are:

1. Direct stimulation of nerve fibres innervating the nociceptors and mechanoreceptors, eliciting either vibration, pressure or pain sensations.
2. Overstimulating of nerve fibres thereby maintaining them in a constant, or near constant, state of depolarisation resulting in a paraesthesia effect (the sensation arising due to the inhibition of the basal neural pulse train, commonly known as "pins and needles").

It is very difficult to estimate the perceived stimulus intensity from theory alone, since the mechanisms of perception of ETS vary according to so many parameters (amplitude, pulse width, pulse repetition rate etc., see below for details). Even though there is significant data already available in the literature, it is essential that the values of the parameters relating to perceived stimulus intensity levels are based on in-vivo testing. In implementing embodiments of the present invention in-vivo testing was performed using the MB1 configuration prior to use in a 2012 clinical investigation, and data was gathered electronically during them. Further in-vivo tests were also performed on the MB2 configuration as part of the design and clinical validation processes.

Somatosensory Stimulation Amplitude Control

Global amplitude control is essential in order to accommodate the natural variation in physiological, physical and genetic factors affecting the sensitivit), conductivity and perceptual characteristics of the patient population including The age of the subject The dryness of the mucosal surface the electrodes make contact with The concentration of ions in the mucosal surface fluid Genetic and physical variations, such as relative thickness of the epithelium layer.

Medium term and long term adaptation

In order to compensate for the sensitivity variation, it is therefore necessary to include a method of stimulation amplitude control so that the intensity of stimulation can be adjusted per patient. The amplitude may be under direct control of the patient to they adjust the intensity to a comfortable level, for example by adjusting the controls on the Control Device, 101.

In a preferred embodiment, the system described herein also includes stimulation amplitude control so that the intensity of stimulation can be adjusted per patient. There are several methods by which the perceptual stimulus intensity can be varied, by controlling the values of stimulus parameters including:

1. The energy of the individual stimulus pulses either by varying the
   Voltage/current magnitude of the pulses
   Width of the pulses
   Polarity of the pulses (anodic versus cathodic)
2. The number of consecutive pulses within the multisensory window of simultaneity (typically no more than 50 ms for auditory-somatosensory).

Of the remaining methods of intensity control (pulse width/pulse amplitude and number of consecutive pulses), it is the number of pulses that is used to vary the amplitude of the stimulus at a high temporal resolution, to increase the effective bandwidth of the stimulus.

MB1 Configuration Amplitude Control

In the current MB1 configuration, a design decision to implement this global stimulation amplitude control was to vary the voltage of the electro tactile pulses. This limits the cost and complexity of the device by requiring only the control of the supply voltage to the ETS drive circuits.

The minimum number of steps required for global stimulus amplitude control is dictated by two parameters:

The just-noticeable difference for amplitude discrimination of electrical stimulation on the dorsal anterior region of the tongue in humans The standard deviation of perceptual intensity due to electrical stimulation on the dorsal anterior region of the tongue across the patient population The overall dynamic range for electric tactile stimulation of the dorsal anterior region of the tongue has been found to be 17.39 dB (SD=2.3 dB), where the dynamic range is defined as the difference between the intensity at the threshold of discomfort and the intensity at the threshold of perception. The corresponding JND within this range was found to be 12.5% of the dynamic range on average, such that 8 different amplitude levels could be discriminated between the threshold of perception and the threshold of discomfort (~2.4 dB per step), but as low as 1.5 dB per step for certain parts of the perceptual range. In addition, the range of perception threshold varied by 10 dB across all 8 subjects in the experiments. Taking the lower step size of 1.5 dB, and dividing it into the total required range (17.39 dB+10 dB) results in a minimum of 18 steps required.

Accordingly, there are 18 global stimulus amplitude levels in the MB1 design, approximately linearly spaced in terms of energy delivery, but with the lowest non-zero level at a raised pedestal (because lower energy levels were below the threshold of perception for all 5 subjects tested during in-house psychophysics experiments on the MB1 device).

The pulses on the MB1 were constant width (17.7 us), and the voltage varied according to the amplitude setting (under the control of the patient), i.e. basing the stimulus drive circuit on voltage-mode control. The voltage levels utilised, along with the resulting volt-second product (potential to depolarise) are detailed in the table below.

MB2 Configuration Amplitude Control

In the current MB2 configuration, electronic design and economic constraints lead to a pivot in the method for adjusting global amplitude, where the global amplitude is controlled primarily by varying the pulse widths (and maintaining pulse voltage amplitude over a more restricted range).

This change to the somatosensory electrode drive circuit is due to the necessity to migrate the electrode drive circuit from the Control Device to the Intra-Oral Device. This necessity stems from fact that the passive IOD in the MB1 required a 32-core cable from it to the Control Device. The cost of this cable and associated connectors is very high, and the reliability and flexibility of the arrangement is less than optimal. Moving the electronic drive circuit from the Control Device to the IOD in the MB2 design results in a lower cost and higher reliability product.

Due to practical constraints, the MB2 is based on a low cost microcontroller unit (MCU), with its outputs capacitive coupled directly to the electrodes. This electronic drive circuit change requires that the drive voltage level in the MB2 be limited to between 4.35V (so a low cost boost converter can be used from a 4.2V Lithium Polymer battery), and 5.85V (just below the absolute maximum supply voltage limit of the MCU), whereas in the MB1 it is adjustable from 3V to 11V. This requires that the range of pulse widths in the MB2 design be increased to compensate for the change in range of the pulse voltage. In particular, to maintain equivalency between the stimulation in the MB2 relative to the MB1 configuration it needs to be assured that the pulse energy levels, at maximum stimulus amplitude settings, subjectively yield at least the same perceptual intensity, and that the lower stimulus levels subjectively yield at least as low a perceptual intensity.

Design of the ETS Stimulus Patterns for the MB2 Configuration.

Given the constraints above, there are two potential candidates for the ETS pulse profiles
1) Use one pulse slot per electrode per frame, and vary the pulse width of the pulses as a function of the global stimulus amplitude AND the dynamic amplitude level
2) Use 8 pulse slots per electrode per frame, as in the MB1 configuration, and vary the pulse width according to the global pulse width setting.

In the case of option 1, the maximum pulse width would be 23.2196 ms/32 electrodes=725.6 us That is far too long for the current hardware to support, since there is a physical limit on the size of the electrode series DC blocking capacitors (currently the limit is about 100 nF). Pulse widths longer than 100 us will result in the 100 nF series capacitor being more than 20% discharged by the end of the pulse, and so 100 us is a realistic upper limit for the pulse width. Also, longer pulses will increase the risk of irritation and sensitisation to the mucosal surface due to electrolysis by-products under the electrodes, because the longer the first phase of the pulse the less the by-products of the electrolysis reaction will be reversed by the 2nd phase (opposite polarity phase) of the pulse.

Additionally, from an energy perspective, a 100 us pulse should deliver significantly more energy (neglecting the effect of the DC blocking capacitors) than the 17.6 us pulses used in the MB1 configuration.

Going for option 2) above, it is required to squeeze 8 pulse slots for each of the 32 electrodes into the frame period.

The requirement is to set the lowest (non-zero) pulse width to achieve the same charge injection as the lowest amplitude setting on the MB1.

On the MB1, the volt-second product was 17.7 us*3V=53.1 Vus

On the MB2, with the voltage set to 4.35V, the lowest pulse width required is therefore $PW_{min}$=53.1 Vus/4.35V~=12 us As indicated in the note above, the maximum pulse charge for the MB2 was required to be higher than for the MB1, and a value of 66% higher is used. This equates to $PW_{max}=V_{max(MB1)}*PW_{MB1}*1.66/V_{MB2}=$ 10.9V*17.7 us*1.4/4.35V~=78 us In practice, to accommodate for patients that have very high sensitivity, two steps are added below the 12 us level, and the remaining number of steps (15 of) are extended to 78 us, with a slightly exponential curve.

The ETS pulse width can be modified to one of several discrete settings (18 in total, to cover the MB1 range of 18 step), as set out in the table below. Based on feedback from patients using the MB2 device (n=120), in three instances there were situations where the patient could perceive the somatosensory stimulus only weakly even with the level set to maximum. To cater for such patients, an additional 3 steps are included at the top end to extend the range. These additional steps are accommodated by incrementing the pulse voltage (from 4.35V to 4.85V to 5.35V to 5.85V) while keeping the pulse width at the maximum of 78 us. These additional steps are shown in FIG. 19.

The pulse width is under the direct control of the patient. For example, it may be adjusted by pressing stimulus amplitude control buttons e.g. (UP/DOWN button pair) on the Control Device 101.

Somatosensory Stimulation Dynamic Amplitude Control

Dynamic amplitude control of the somatosensory stimulation is useable as a means of encoding the relative amplitude of the audio stimulus from which the somatosensory stimulus is derivable. It will be appreciated that this facilitates greatly increasing the information rate of the somatosensory stimulus, so that it can more closely match the information rate of the audio stimulus from which it is derived.

The increase in information rate that can be achieved is essentially limited by the somatosensory perceptual dynamic range of the human tongue.

Previous studies on ETS of the human tongue has shown that the typical perceptual dynamic range is of the order of 17.39 dB+1-2.3 dB from minimum perception threshold to maximum level without discomfort. It was also found that the average Just-Noticeable Difference (JND) for amplitude discrimination is about 2.4 dB (Lozano, Cecil A., Kurt A. Kaczmarek, and Marco Santello. "Electrotactile stimulation on the tongue: Intensity perception, discrimination, and cross-modality estimation." *Somatosensory & motor research* 26.2-3 (2009): 50-63). Therefore about 8 discrete amplitude steps (not including zero) are all that is required to represent the full perceptual dynamic range.

Each of the three methods by which the perceptual amplitude of the tactile stimulation can be modulated are detailed in the following table:

TABLE 6

| Method of dynamic amplitude control | Suitability | Notes |
|---|---|---|
| Pulse Voltage/Current Modulation | Low | Dynamically adjusting the voltage/current level on a per-pulse basis was ruled out as a viable option in the MB1 and MB2 designs, as it would have increased the complexity and cost of the drive electronic circuit by an order of magnitude. Future incarnations of the technology may utilise this approach however. |
| Pulse Width Modulation | Medium | Dynamically adjusting the pulse width on a per- pulse basis in the MB2 was ruled out because this means of control was reserved for the global amplitude control (to allow the patient to control the stimulation to their level of comfort). |
| Pulse Count Control | High | Dynamically adjusting the pulse count was deemed the most appropriate method of dynamic amplitude control for the following reasons: The dynamic range of 17.39 dB in 8 discrete steps is feasible, given the frame rate and number of electrodes (see below) It mitigates the need for expensive, space hungry and power hungry electronics to drive the electrodes It retains the ability to adjust the pulse width as a means of global stimulation amplitude (which requires at least 17 discrete steps, see above). |

Method of Pulse Count Control

Pulse count control is achievable in practice by simply varying the number of electrical pulses on any given electrode, in any given frame. This corresponds to a discrete number, or count, of pulses in a burst, where the burst is shorter than the analysis frame length. As long as the duration of the frame is less than or equal to period of sensory integration (period of tactile simultaneity), the pulses are wide enough to depolarise the nerve fibres, and the pulses are spaced far enough apart (i.e. that the neurons can re-polarise in time before the next pulse), the perceived amplitude of the stimulus is proportional to the number of pulses up to and including 6 or 7 pulses (J Kaczmarek, Kurt, John G. Webster, and Robert G. Radwin. "Maximal dynamic range electrotactile stimulation waveforms." *Biomedical Engineering, IEEE Transactions on* 39.7 (1992): 701-715).

Temporal Transformation of Audio Frequency Components to Somatosensory Stimulus

FIGS. 8 to 14, inclusive, serve to illustrate the transformation between audio and somatosensory stimulation, but is generalised in terms of the number of frequency bins (n) and the number of quantised amplitude levels (q).

These figures illustrate how one of the binaural channels is transformed for use in a split-array stimulator topology. For the unified-array stimulator topology used in the MB1 and MB2, the left and right audio channels are mixed prior to the transformation (with the audio kept as stereo for delivery to the patient via the headphones).

As an example only, the pulse pattern is illustrated for one electrode only (electrode #3 in this case, which corresponds to frequency bin #3).

As per the requirements above, the audio to somatosensory transformation process implementable for both the MB1 and the MB2 is summarised as follows:

The stereo audio signal for the entire treatment session (typically 30 minutes of audio) is first
  converted to monaural, by summing the left and right channels and then normalizing for the single array embodiment OR
  For the split-array embodiment, the audio is normalised without converting to monaural.
The resulting audio is then divided into overlapping sections of duration $t_w$, corresponding to twice the frame duration, $t_p$
A Blackman tapering (window) function is then applied to each of the audio sections
Then a time→frequency transform is computed on each of the windowed audio sections, to yield frequency domain signals
  For the MB1 and MB2, a discrete Fourier transform is useable, however gammatone filters or wavelet transforms can be used in alternative embodiments.
The resulting frequency domain signals are further analysed according to the predetermined frequency bins (e.g. as per the Bark scale critical bands as outlined above), to yield an array of n magnitude values such that each magnitude value corresponds to the amplitude of the frequency domain signal for the each of the individual frequency bins.
The array of magnitude values are normalised according to the peak values across the entire set of signals for the whole treatment session, so that for each frequency bin, the magnitude values are normalised to the maximum level.
The resulting normalised magnitude values are further quantised into q discrete levels.
The resulting quantised signals are stored in a way that they can be used to control the number of pulses for each frequency bin (mapped to an individual electrode) within each frame period, $t_p$.

In order to implement this transformation in practice, several parameter values that are used in the MB2 and MB1 must be chosen including:

The frame period, $t_p$

The pulse slot period, $t_{ps}$ which also dictates the maximum ETS pulse width, $t_{pw}$ The audio sample rate, $F_s$ The following sections detail the rationale, constraints and calculations from which these parameter values are defined for the MB1 and MB2 devices.

Optimal Temporal Resolution Calculation

There are several factors to be considered when calculating the optimal temporal resolution of the transformation from audio to tactile stimulation. Many of these factors have already been elucidated in the sections above, these are outlined in the following tables 7 and 8:

TABLE 7

| Parameter | Physiologic Parameter Value | Impact/Constraint on Design of Transformation |
|---|---|---|
| The maximum refractory (re-polarisation) period for somatosensory nerve fibres in the dorsal anterior region of the tongue resolution | 2 ms** | The minimum period between pulses on the same electrode must be greater that this period. |
| The perception of tactile simultaneity in humans (the effective window over which our perceptual centres integrates tactile stimulus) | 30 ms* | If the mechanism of action (MOA) is primarily at cortical levels, then the frame period should be longer than this period, so that each somatosensory frame does not blur into adjacent frames. If the MOA is primarily at sub-cortical levels then this need not be an upper limit for the frame period. |

*Geffen, Gina, Virginia Rosa, and Michelle Luciano. "Sex differences in the perception of tactile simultaneity." Cortex 36.3 (2000): 323-335.
**Burgess, PR T., and E. R. Perl. "Cutaneous mechanoreceptors and nociceptors." Somatosensory system, Springer Berlin Heidelberg, 1973. 29-78.

TABLE 8

| Parameter | MB2/MB1 Parameter Value | Impact/Constraint on Design of Transformation |
|---|---|---|
| The number of frequency bins to be represented via somatosensory stimulation | 32 | The frame length should be long enough to accommodate the product of The number of frequency bins AND The number of pulses per frame (for dynamic range control) at the maximum pulse width, such that there are no temporally overlapping pulses. |
| The centre frequency of the lowest frequency bin to be represented via somatosensory stimulation | 545 Hz | The frame length should be long enough such that there are at least two periods at this frequency (4 periods including the window function), i.e. minimum frame length of 4/545 = 7.4 ms |
| The maximum pulse width required to ensure strong stimulus percept | 17.7 us (MB1) 78 us (MB2) | The pulse slots must be long enough to accommodate pulses of these widths |
| The required dynamic range of the tactile stimulus and the number of discrete amplitude steps required within that range | 8 | The frame length should be long enough to accommodate the product of The number of frequency bins AND The number of pulses per frame (for dynamic range control) at the maximum pulse width, such that there are no temporally overlapping pulses. |

In addition, several other factors constrain the design of the auditory to somatosensory mapping including:

The nature and design of the electro-tactile stimulation electronics (the IOD electronics).

The maximum pulse energy level that the electrodes can tolerate before significant corrosion sets in due to galvanic action instead of faradic action.

The available voltage, or energy, per pulse (a function of the electronic design topology)

The audio sample rate of the original auditory stimulus from which the somatosensory stimulus is to be derived.

Electrode Topology

In both the MB1 and MB2 configurations the electrode topology is configured in accordance with a number of considerations. In order to reduce the total number of electrodes, and ease the complexity of the drive electronics, the MB2 and MB1 are designed such that the same electrodes also act as the return path electrodes. In other words, a dedicated return electrode is not necessitated, but rather to configure all electrodes apart from the active electrode at a particular point in time to act as joint return electrodes. One consequence of this is that there is less scope for overlapping (simultaneous) pulses—the ideal stimulation paradigm is to have no overlapping pulses, i.e. that only one electrode is ever active at a particular point in time. This ensures that all other electrodes can be configured as the return path for the stimulus current, and with 32 electrodes in total, there will be 31 for the return path. This results in the highest electric field strength directly beneath the active electrode, with a fraction of that field strength under the adjacent (return) electrodes. When the stimulus energy level is set correctly, only nerve fibres within a small spread region surrounding the active electrode will be activated. However, if the stimulus energy level is set too high, then there is the chance of stimulating nerve fibres under adjacent electrodes.

Temporal Resolution Calculations

Pulse Slots

To maintain synchronization with the audio data, one consideration is that the somatosensory pulses should occur at the same timing resolution as the audio samples, i.e. at a resolution of $1/44100$ s (22.6 uS). To accommodate this, the time axis is divided up into "Pulse Slots" of period $t_{ps}$.

It was determined through validation experiments that a pulse width of 22.6 us was more than enough, even at low drive voltages, to fire the sensory nerves in the tip of the tongue. However, it was also found during validation that that the resulting number of electrotactile pulses gave a very strong, sometimes unpleasant sensation. Another constraint or consideration that places a lower bound on the pulse slot interval is related to the neural repolarisation period (2 ms).

Allowing for 25% headroom, and since there are 32 electrodes to be serviced, the associated pulse slots can be spread out to cover the entire 2.5 ms repolarisation period. Therefore the minimum pulse slot period should be 2.5 ms/32=78 us. The next highest period value that is also a multiple of the audio sample rate is 90.7 us, which results in a pulse slot for every 4 audio samples. So the pulse slot period, $t_{ps}=4/44100=90.7$ us. In practice, there needs to be some dead time between pulse slots, as the microcontroller that generates the pulses will have some overhead. It has been experimentally verified that pulse widths of up to 78 us are possible with a low cost 16 bit MCU running at 0.5 MIPS even when the pulse slot period $t_{ps}=90.7$ us. Therefore, this choice of $t_{ps}$ is suitable for use in the MB2, which requires the MCU in the IOD to be low cost and energy efficient.

Calculating Frame Period

In calculating the minimum frame period the following constraints or considerations are taken into account. Each frame must be able to accommodate 8 pulses (dynamic amplitude), times 32 electrodes times the pulse slot period (90.7 us). Therefore, the frame period $$t_p = n*q*t_{ps} = 32*8*90.7 \text{ us} = 23.219 \text{ ms}$$

Where $t_p$=the frame period.
n is the number of electrodes (32)
q is the number of amplitude bins that the amplitude is quantized to (8)

Since 32 pulses can occur for each pulse slot within a given frame period, the inter-pulse period on any given electrode must be a minimum of $$t_{ipp} = t_{ps}*n = 90.703 \text{ us}*32 = 2.9 \text{ ms}$$

This is greater than the nominal repolarisation period of 2 ms, and so meets the critical requirement that subsequent pulses on any given electrode only occur after the nerve fibres have had sufficient time to repolarise following the previous depolarisation.

Pulse Slot Timing

Figure 6:
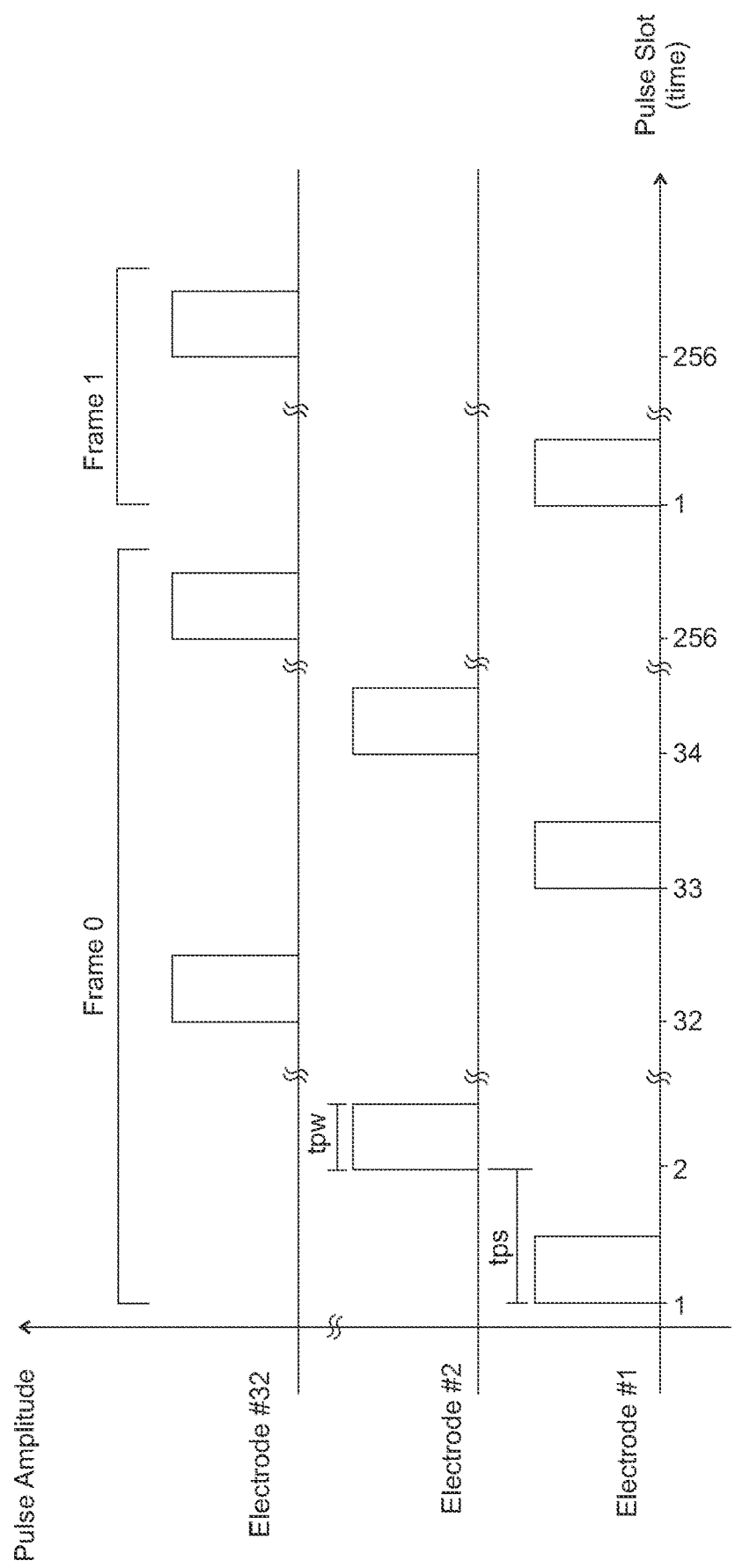
FIG. 6 is an overview of electro-tactile stimulus patterns in accordance with an aspect of the invention

Based on the parameter values, the time pattern of the tactile pulses are generated. There are a total of 256 pulse slots per frame. Each electrode is assigned a subset of the available time slots as diagrammed in FIG. 6. This figure outlines the pattern of pulse slots for a single frame (frame 0), and a follow on frame (frame 1).

The total number of slots that an electrode is set active in any given frame is determined by the amplitude of that frequency bin in the frame. For example, if the amplitude level is 2, then the first two slots for the electrode are set active and the remaining are kept de-activated. In the example shown in FIG. 6, there is 8 pulses for each of electrodes #1, #2 and #32 in Frame 0.

ETS Pulse Morphology

Figure 14:
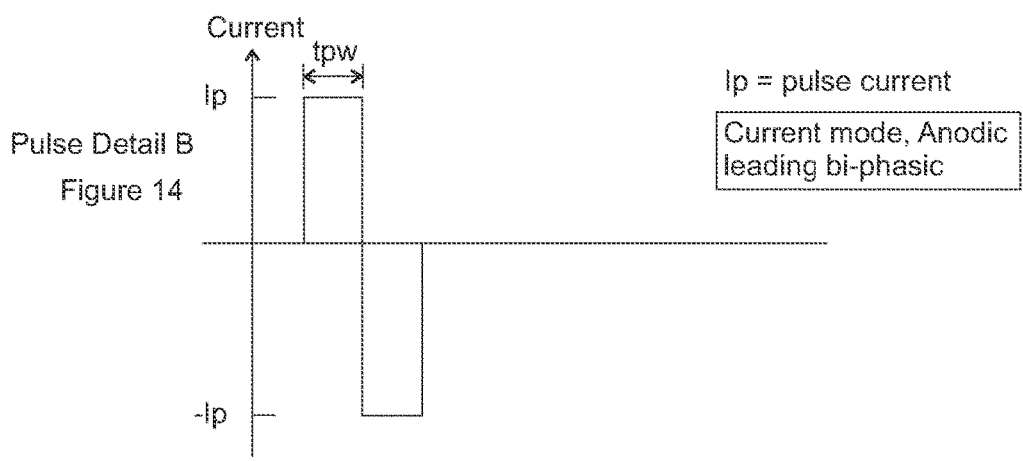

It will be appreciated that the MB1 and MB2 configurations use pseudo-biphasic, anodic (positive leading) pulses, as diagrammed in "Pulse Detail B" of FIG. 14.

Pseudo-biphasic pulses are generated using a rectangular wave voltage source, with a series capacitor to the active electrode. Because the net charge across the capacitor always sums to zero (an ideal capacitor has infinite impedance to direct current), the pulse is effectively bi-phasic. This results in minimal electrolysis products generated at the electrode/mucosal surface interfaces, thereby maintaining the integrity of the electrodes and minimising the risk of sensitisation or iteration to the patient.

Results of in-vivo experiments with anodic pulses demonstrated a significant reduction in the threshold of perception for anodic pulses rather than for cathodic pulses. Accordingly, anodic pulses are implemented in accordance with the embodiments described herein however it is not restricted as such.

ETS Pulse Mode Control

For electro-stimulation there are two principal methods of control, namely

Voltage mode control

Current mode control

The relative advantages and disadvantages of each are outlined in Table 9:

| Stimulation Source Type | Advantages | Disadvantages |
| --- | --- | --- |
| Voltage sources | Low cost and complexity to implement Less exposure to hazardous energy density in the event that the electrodes become partially disconnected | More difficult to control the injected charge, especially if the contact area and contact electrolytes have a tendency to vary over time |
| Current sources | High degree of control of the delivered charge | Potential for exposure to hazardous energy density in the event that the electrodes become partially disconnected, particularly for transcutaneous stimulation on dry skin using electrodes with large surface area. High cost and complexity to implement |

Even though current mode control is preferable in many scenarios, it will be appreciated that due to the necessity for stimulating the mucosal surface of the tongue, voltage mode control is preferable for the following reasons:

Reduced risk of 'startle' hazards, for example in a scenario where the electrodes temporarily break contact from the mucosal surface, the voltage increases to compensate, and when the electrodes make contact again the higher voltage causes an initial 'shock' before the current-mode control loop re-stabilises.

The availability of a constant electrolyte (saliva) results in a stable electrical interface, partially offsetting the need for current-mode control.

The cost and complexity of a 32-channel current mode control circuit would be significant compared to a voltage mode control circuit.

Current Mode Control of Stimulation Pulses

In the MB1 and MB2 configurations described herein the stimulation is assumed to be voltage-mode control, however, it will be appreciated that current mode control can also be used. Based on in-vivo tests, at 50 us pulse width, the voltage on a 47 nF series blocking capacitor dropped from increased from 0V to 1.35V on average across all users. The required current is therefore $$I = CdV/T, dV \sim = 1.35V*47 \text{ nF}/50 \text{ us} = 1.27 \text{ mA}$$

So, if constant current mode control is used instead of voltage mode control, then a constant current of 1.27 mA should be used, with the voltage limited to anywhere between 6V and 12V.

The range of charge delivered in this scenario will be from $Q(min)=I*T\ min=1.27\ mA*5\ uS=6.35\ nC$ to $Q(max)=I*T\ max=1.27\ mA*78uS=99nC$ A potential disadvantage with the audio to somatosensory mapping described above in relation to the configurations proposed for the MB2 and MB1 configuration is that there may be significant temporal smearing of auditory events when transformed into the somatosensory signals, particularly at higher frequencies, because:

The analysis windows are fixed at 23.2 ms, for all frequency bands

There is 50% overlap in the analysis windows (to cater for the application of window functions prior to computing the Fourier transforms)

The amplitude of the auditory events is mapped to a train of pulses rather than a single pulse, and therefore the somatosensory event that is derived from an auditory event can be spread over a period of up to 8 pulses at up to 2.9 ms inter-pulse interval (i.e. spread over a temporal window of duration up to 20.5 ms).

In practice, this results in correlates of high frequency auditory events being up to +/−μms shifted in time with respect to the first pulse of the corresponding somatosensory events, where the time shift has a truncated normal distribution.

An alternative transformation is outlined below, which breaks away from the temporal-frequency resolution trade-off limitations of standard Fourier analysis, by analysing each frequency band at a rate that is commensurate with the centre frequency of that band, i.e. by analysing each frequency band at a different rate in order to reduce temporal smearing of the result.

FIGS. 18 and 19 below shows the high level block schematic and timing waveforms of the alternative transformation.

The schematic shows just two of the n frequency channels of the transformation, and for one side of the split-array configuration only. In this regard, only the left audio channel is shown. The auditory stimulus component (including the mechanisms relating to the spectral modifications and amplitude adjustment) is not shown in this schematic, as it is the same for the MB1 and MB2 configurations detailed above.

The timing diagram indicates the typical timing for one of the n channels. Two analysis frames are shown as an example, the first frame indicates a scenario whereby there is sufficient energy in the relevant frequency band to cause a somatosensory pulse to be generated, whereas in the second frame there is insufficient energy and hence a somatosensory pulse is not generated.

The band pass filters are designed such that they have centre frequencies and bandwidths as per the Bark scale critical bandwidths. A gammatone filter bank would be suitable in this regard, as the filter response closely matches the response of the basilar membrane in the cochlea.

The algorithm operates as follows:

The audio signal to be transformed is split into n different branches, one branch for each of the somatosensory channels (frequency bins).

The signal passes through a band-pass filter, with centre frequencies' preferably at the Bark scale critical band centre frequencies.

The signal is then rectified (i.e. the absolute value is computed).

The rectified signal is then integrated over a period, $t_{f[x]}$, in order to calculate the energy of the signal within that period.

The integral signal (Iout[x]) is compared to the threshold level, Threshold[x], in the comparator, where the output of the comparator transitions high once the integral signal magnitude is higher than the threshold value and vice versa.

A D-type flip-flop is used to generate the somatosensory pulse based on the comparator output (Cout[x]) and two pulse slot timing signals, PulseSet[x] and PulseReset[x], where a pulse is generated with the appropriate pulse width if, and only if, the comparator output is high at the instant in time when the pulse slot starts (i.e. at the instant in time when the PulseSet[x] signal transitions high).

The timing signals, IntReset[x], PulseSet[x] and PulseReset[x] are arranged such that There is no overlap in pulse slots associated with electrodes that are topographically adjacent to each other (this is to assure that every pulse presented to an electrode has all adjacent electrodes to said electrode available as the current return path).

In one version of this implementation there is never any overlap in pulse slots (as is the case for the MB1 and MB2), in which case all but one of the electrodes can take the role of the return current paths.

In another version of this implementation, there is overlap in pulse slots but only with respect to pulses that are destined for electrodes that are not topographically adjacent to each other. In practice, a maximum of 2 to 4 simultaneous pulses can be supported without violating this non-adjacent requirement.

The analysis period (frame period $t_{f[x]}$) must be greater than the somatosensory refractory period (which may be of the order of 1 ms to 2.5 ms, the actual value must be elucidated by in-vivo experiments). This is to avoid the possibility of subsequent pulses occurring before the target nerve fibres have repolarised following the previous pulse.

The analysis period (frame period $t_{f[x]}$) should also be greater than the impulse response of the auditory filters. For example, if using gammatone filters, the impulse response can be represented in about 10 cycles of the filter centre frequency and therefore the analysis period should be greater than this.

The analysis period (frame period $t_{f[x]}$) should also not be substantially greater than the impulse response of the auditory filters, as this will unnecessarily sacrifice temporal resolution of the transformation. For the higher frequency bands however it is expected that the refractory period will be the limiting factor in relation to this.

To maximise the period of integration within a given analysis window, the PulseSet[x] signal should occur as close to the end of the analysis window as possible (e.g. still leaving enough time for the pulse Q[x] to complete before the next analysis window starts, although it is also feasible for the pulse to continue into the next analysis window period).

The analysis windows can be temporally consecutive, or they can overlap. For the lower frequency bands where the analysis period, t $t_{f[x]}$, is greater than twice the refractory period it is preferable that the windows overlap, as this improves the temporal resolution in these bands. At the higher frequency bands were the analysis period is less than twice the refractory period it is preferable that the analysis windows are temporally consecutive. The timing diagram below only shows an example where the analysis windows are temporally consecutive.

The global delay between the auditory and somatosensory stimuli can be configured by setting a delay on the audio signal to the patient (if it is required that the somatosensory stimulus leads the auditory stimulus), or by including a delay line in the somatosensory signal lines (Q[x]) if it is required that the auditory stimulus leads the somatosensory stimulus.

The transformation can be implemented in either the analog or the digital domains, since there are no elements of the system that requires a digital signal processor. However, it will be appreciated that in order to reduce the associated electronics cost, it would be preferable to implement the transformation in the digital domain.

The timing signals, IntReset[x], PulseSet[x] and PulseReset[x], where $x \in \{0:n-1\}$ must be generated with low jitter, and as such this implementation is more amenable to a digital implementation.

It is possible that this transformation is performed either offline, as would be the case in the MB2 configuration, or online. The advantage of the former is that the implementation is lower power, and will extend the battery life in portable embodiments of the system. The MB2 configuration of the system can be programmed to implement this transformation by software changes alone.

In an exemplary arrangement of this alternative configuration, the optimum analysis window lengths for each listed frequency bin (filter) while meeting the constraints outlined above is shown in FIG. 20. In this example:

The repolarising period is assumed to be 2.5 ms, and so the resulting transformation will not output a subsequent pulse on the same electrode until this time has elapsed.

The filters chosen are gammatone filters, with centre frequencies the same as the Bark scale critical bands as utilised in the MB2 split-array configuration. In this case, the gammatone filters are truncated to a length of 10 periods of the relevant filter centre frequency.

The analysis window length varies according to the filter frequency, however they are set to integer multiples of the minimum repolarisation period. This is to ensure that the temporal arrangement of the pulses can be such that the pulse overlapping requirements are met (see above).

The analysis window shift (i.e. the period that the analysis window shifts for each analysis step) is set such that it is greater than or equal to the refractory period, and greater than 2.5 periods of the filter centre frequency.

As can be seen in this example, the temporal resolution of the transformation increases as the audio frequency increases. The temporal resolution is limited only by the minimum repolarisation period for the somatosensory modality being utilised, or for the lower frequencies by the length of the impulse response of the filter. In certain circumstances, this repolarisation period may be 1 ms or lower, which would facilitate even higher temporal resolution for the higher frequency bands than that achieved in the above example.

System Overview

Figure 7:
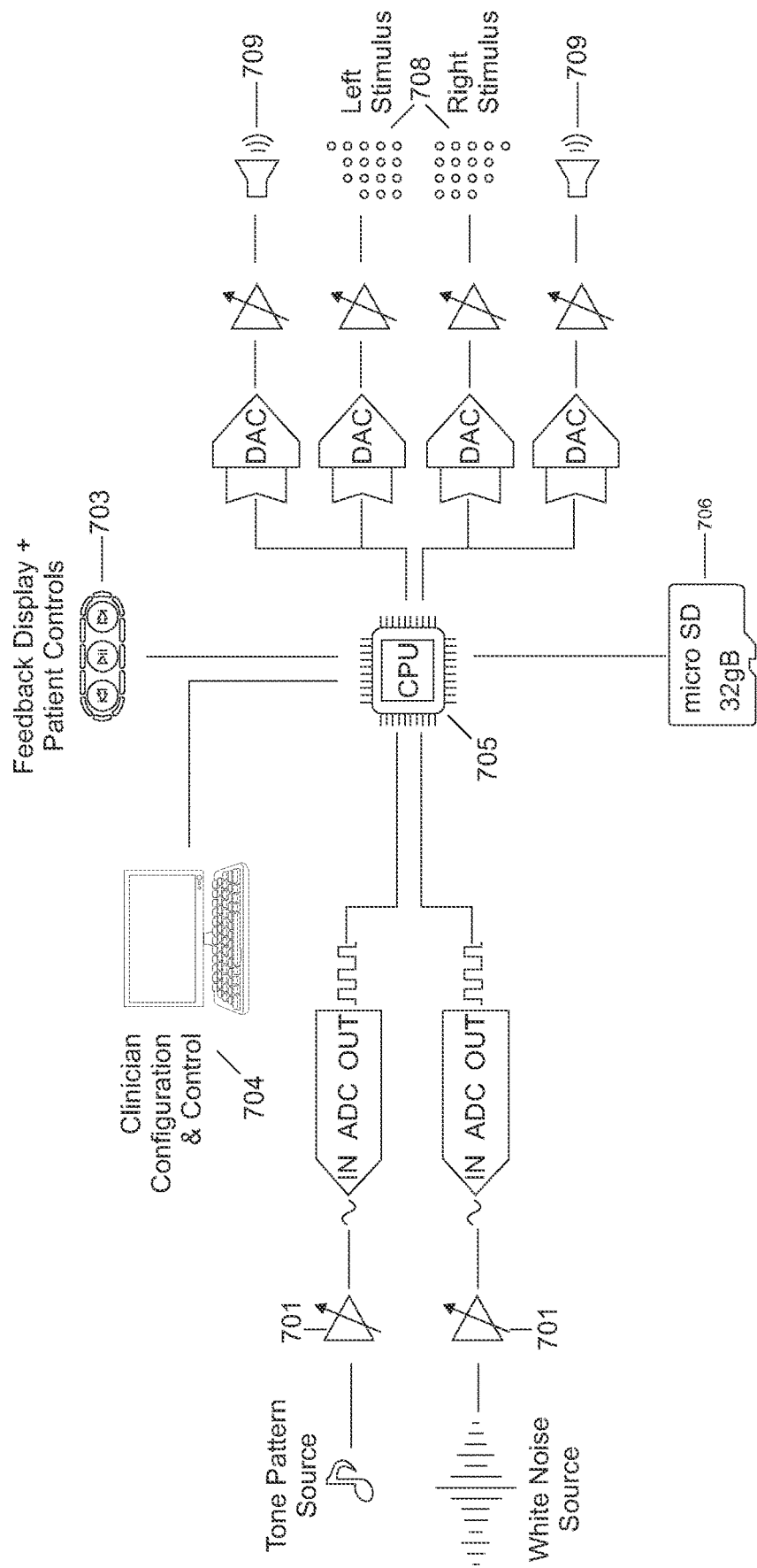
FIG. 7 is a sample diagram of a microcontroller implemented system in accordance with an embodiment of the invention.
Figure 12:
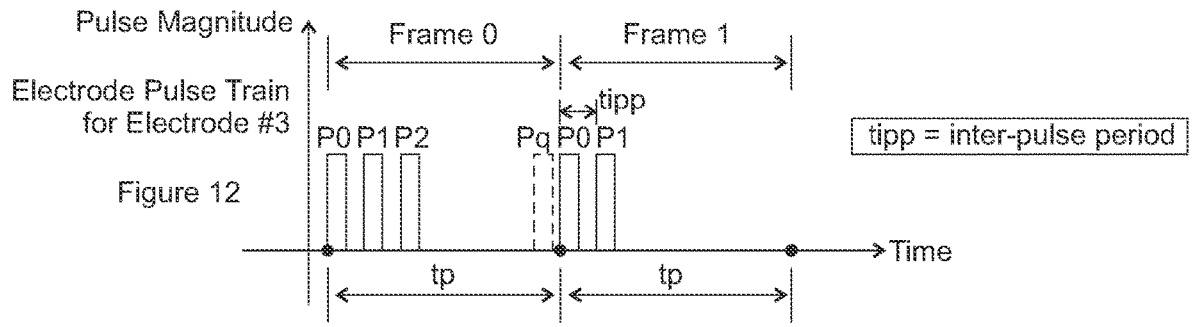
Figure 13:
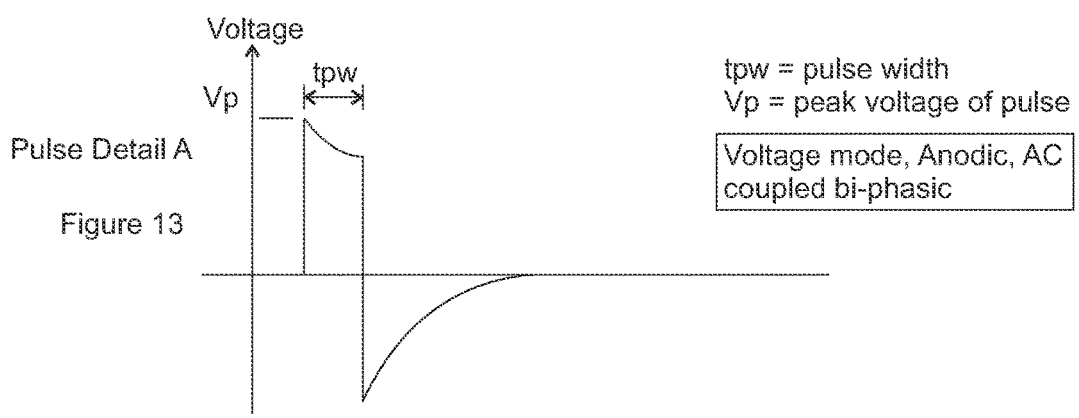

An overview of a system in accordance with the invention is shown in FIG. 7. The dual audio inputs as described above is sampled by the central processing unit, CPU, 705, wherein said audio inputs can be mixed digitally and further spectrally modified for output to the auditory stimulation unit, and one or more of the audio inputs are transformed to the somatosensory stimuli as described above. It will be appreciated that this CPU may be any computing device such as an embedded microcontroller, an FPGA, a personal computing device (phone, tablet, PC etc.). Once the transformation is complete, the resulting data can be stored to the local memory, for example the micro SD card, 706, to save energy of having to re-transform the audio for subsequent treatment sessions. It will be appreciated that other memory devices may be used. The CPU transforms the audio into the required somatosensory stimulus, and displays this stimulus on the somatosensory stimulus arrays 708 in synchronisation with the audio, 709, which is delivered through a set of headphones (though bone conduction transducer, loudspeakers, hearing aids or cochlear implants or other audio transducers can also be used as described above). Key parameters relating to the delivery of the stimulus to the patient are recorded to file and stored on the memory, such as the card 706. These parameters include, but are not limited to, the following:

Duration of use

Time and date of use

Identification data (hardware serial number, software versions) for tracing results to unique patients Stimulus parameters Energy measurement of stimulation Audio stimulation level settings Somatosensory stimulation level settings Audio track selection (for multi-track systems)

Also provided is a user interface for providing feedback to the patient, 704, such as a keyboard, touch screen interface, mobile computing device interface, computer application or the like which would facilitate a clinician interacting with the system so as to configure key parameters, such as:

Filter settings, as per the patients audiogram or tinnitus match frequency

Audio volume pan control, as per the patient's audiogram.

In addition to this clinician interface, a patient interface 703, is also provided to allow the patient to adjust the stimulus levels and the start and end of the treatment sessions. Events such as low power or low battery may also be reported to the patient. Again this may be any visual or haptic display and may include visual display units, mobile computing devices and applications run thereon or the like.

In the systems described herein the electrode device circuit may be located remote from or local to the Intra-Oral device as outlined in the MB2 and MB1 configurations described above. The principle change in migration between MB1 and MB2 is that a global stimulus level control is preferably controlled by varying the pulse width of the stimulus in the MB2 configuration versus varying the pulse peak voltage level in the MB1 configuration. In the MB2 configuration, the drive voltage may also be lower than that in the MB1 configuration. For example, in the local or MB2 configuration the drive voltage level may be fixed at between 4.2V and 5.8V, whereas in a remote or MB1 configuration the drive voltage may be adjustable from 3V to 11V. This requires that the range of pulse widths in the local implementation will have to be increased to compensate for the change in range of the stimulus voltage.

It will be appreciated that the MB2 configuration wherein the control is located local to the stimulator array provides an efficient hardware design it is further reliable. For example, in such a configuration it is possible to use a 4 pole connector (e.g. a micro-USB connector) to connect to the signal processing controller rather than a 32-pole connector where the stimuli are generated remote from the array. Low cost microcontrollers can also be used to avoid the expense and complexity required of the high voltage drive circuitry in a remote configuration.

It will be appreciated that in any configuration, the stimulus generation unit, the auditory stimulation unit and the stimulus array can communicate wirelessly with each other rather than by wired connections. In the MB1 configuration, all components are wired together, in the MB2 configuration the auditory stimulation device communicates wirelessly with the stimulus generation unit.

Clinical Study Tinnitus Alleviation Via Sensory Stimulation

The following material describes the reduction to practice investigation (clinical trial) of MB1 configuration of the tinnitus treatment device. The trial was carried out in a clinical setting with participants suffering from tinnitus in June to September 2012.

Materials and Methods

Subjects

This prospective single arm pilot study was conducted with approval from the Research Ethics Committee of the National University of Ireland, Maynooth and The Hermitage Medical Clinic, Dublin. Self-referred patients that met inclusion/exclusion criteria (see below) were recruited in the order that they presented at the clinic and not pre-selected in any way. Sixty-four participants were screened for eligibility and written informed consent was obtained from 54 suitable participants (19 female; mean=45 yrs, range 28-64 yrs, 35 male; mean=47 yrs, range 21-64 yrs) with subjective, chronic tinnitus. The exact definition of chronic tinnitus varies in the literature but generally refers to tinnitus that has not self-resolved in the short to medium term, i.e. six months, and persistent tinnitus refers to tinnitus that is present every day. Participants were informed that participation in the study was entirely voluntary, and they were free to withdraw from the study at any time without having to give a reason. The recruitment process allowed participants adequate time to fully consider participation. Participation was anonymous. The eligibility of study participants was determined by the following inclusion and exclusion criteria:

Inclusion Criteria:
  Aged <65
  Suffering from persistent, subjective tinnitus for at least the previous 6 months
  Age or noise related sensorineural hearing loss (>25 dBHL in at least one ear).
  Have English reading, comprehension and written skills
  Able and willing to participate in the study for the full 14 week duration
  Informed consent Exclusion Criteria:
  Ulceration of oral cavity or tongue, oral mucosa or significant intra-oral disease—to mitigate risk of further aggravation of these symptoms
  Meniere's Disease—due to the fluctuating hearing loss normally associated with the condition
  Current medical legal cases regarding tinnitus or hearing—in order to avoid any conflict of interest
  Currently undergoing any pharmacological or electrical stimulation-based treatment for tinnitus—in order to accurately measure the independent effect of the intervention
  Pacemakers—due to potential electromagnetic interference Participants who were not deemed eligible at pre-screen to take part in this particular study were referred back to their general practitioner (i.e. primary care physician) and received a formal letter of refusal.

Study Design

This was a 14-week single-arm pilot study to assess the feasibility of auditory and somatosensory bi-modal stimulation and its effect on tinnitus outcome measures. The study population was not powered for significance as this was an observational study. Participants visited the clinic every two weeks for the duration of the study, i.e. 14 weeks (V0 at Week 0, V1 at Week 2, etc.). Participants were screened without any intervention in a clinical setting for the first 3 screening visits, two weeks between each, to establish baseline clinical measures of tinnitus severity (pre-treatment). The participant was not required to perform any tasks in-between these visits. Participants were assessed by employing the most commonly used psychoacoustic and psychometric tinnitus measures including: Minimum Masking Level (MML), Tinnitus Loudness Matching (TLM) and Tinnitus Handicap Inventory (THI). The screening assessments were carried out during periods without any stimulation from the device.

There are several factors outside of the treatment of the condition that can affect the perceived benefit from any treatment of tinnitus. Hesser et al (The effect of waiting: A meta-analysis of wait-list control groups in trials for tinnitus distress. J Psychosom Res. 2011 April; 70(4):378-84) reviewed the response rates of participants on a waitlist for tinnitus treatments and found that participant's distress can reduce over short wait periods. This improvement can be attributed to the attention and reassurance the participant receives from the investigator and/or a knowledgeable professional, factors known to contribute to alleviation of tinnitus symptoms. The screening phase in this study was employed to address improvements in symptom severity achieved due to this anticipatory effect from study participation. Assessment scores from the third screening visit were set as baseline values. It was expected that any improvement from the therapeutic effect of study participation would be mitigated by the third visit.

At the third visit participants were provided with the neuromodulation device to take home for the remainder of the study and asked to use it for between 30 and 60 minutes every day for the next 10 weeks. Participants were shown how to use the device and told to set the audio and tongue stimulation to the most comfortable levels for them. Participants were asked to return to the clinic every two weeks in order to repeat the assessments carried out in the screening period. Where it was not possible for participants to return to the clinic, they completed the paper version of the THI remotely and sent the copy to the investigator site. Participants were advised to terminate device use and to contact the investigator if they experienced any side-effects or adverse events. They were also instructed to contact a member of the research team regarding any device malfunction.

The study was conducted by a clinical audiologist who is registered with the Irish Society of Hearing Aid Audiologists and the Irish Academy of Audiology, under the clinical supervision of a senior consultant otolaryngologist head & neck surgeon who is a member of the Association for Research in Otolaryngology, European Academy of Otology and Neurotology, Royal Society of Medicine: Otology, Laryngology & Rhinology, Prosper Meniere Society, Irish Otolaryngology Society and the American Auditory Society. The same audiologist performed all assessments. Assessment scores were recorded in a paper-based system, meaning the audiologist was not blinded from previous results.

However, the audiologist did not refer to previous assessment scores during evaluation.

Compliance Monitoring and Data Inclusion Criteria

Participant compliance with treatment administration was determined technologically using the data logging function on the device. The following events, along with their date and time, were recorded in non-volatile memory:

Power on/off and treatment start/pause/resume events

Audio volume and somatosensory stimulus intensity settings

Electrical current magnitude delivered via the electrodes (used to determine participant contact)

Battery voltage level

Error events

Participant safety was assessed at each clinical visit.

While there is no definitive prescription for treatment duration, the 10 weeks of treatment employed in this study was based on a similar study of neuromodulation by Tyler et al (Tyler, R., Haskell, G., Preece, J. and Bergan, C. (2001) Nurturing patient expectations to enhance the treatment of tinnitus. Seminars in Hearing, 22, 15-21). In the event that participants did not complete the final assessment, scores from the penultimate assessment were used.

The protocol required participants to use the device for between 30 and 60 minutes a day, 7 days a week. Compliance in this context refers to the number of days over the course of the treatment where the session duration, i.e. how long the device was used continuously, was at least 30 minutes. In clinical studies of pharmaceuticals, participants are considered compliant if their adherence is greater than 80%. The exact durational properties of this treatment are still under investigation and so a somewhat more generous cut off for compliance was employed, i.e. 66%; the cohort was divided into those that are considered 'compliant' and those that are considered 'non-compliant' according to this threshold.

Analysis

The data set for this study consisted of THI, TLM and MML data from 44 participants over 10 weeks of treatment. Data on compliance to study protocol as well as audio and somatosensory stimulation settings used by the participants over the ten weeks was also collected. Participant data was included in the analysis if tinnitus symptom scores were available for baseline (V2) and at least the penultimate visit, and if they had access to the device for at least 8 weeks, i.e. did not return the device early. The analysis in this paper investigates whether any statistical improvement in the three assessments of tinnitus symptoms was observed after 10 weeks of treatment with the device.

THI scores are not normally distributed, so the Wilcoxon signed rank test was employed to test for statistical significance between baseline (V2) and final visit. TLM and MML datasets were found to be normally distributed and a paired t-test was employed to test for statistically significant differences between baseline (V2) and V7. In addition to analysis of statistical difference, the proportion of participants achieving clinically significant differences was assessed. Jastraboff et al (Jastreboff P J, Hazell J W, Graham R L. Neurophysiological model of tinnitus: dependence of the minimal masking level on treatment outcome. Hear Res. 1994 November; 80(2):216-32) reported that a decrease in 5.3 dB on the MML scale significantly correlated to patients reporting improvements in their tinnitus. While Zeman et al (Zeman F, Koller M, Figueiredo R, Aazevedo A, Rates M, Coelho C, Kleinjung T, de Ridder D, Langguth B, Landgrebe M. Tinnitus handicap inventory for evaluating treatment effects: which changes are clinically relevant? Otolaryngol Head Neck Surg. 2011 August; 145(2):282-7) demonstrated that a 7 point drop in THI score also reflects a clinically significant improvement. No clinically significant reduction for TLM could be found in the literature so the 5.3 dB for the MML was employed. The participants were classed as improvers or non-improvers based on the differences in their symptom scores from baseline (V2) to V7 in reference to these values for clinical significance.

The log files provided information on device usage as well as stimulus levels over the course of treatment for both auditory and somatosensory stimuli. Secondary analysis examined patterns of auditory and somatosensory stimulus to investigate any insights into participant's usage of the device.

Study Registration

The Research Ethics Committee of the National University of Ireland, Maynooth or the Hermitage Medical Centre did not require registration to a clinical trials registry prior to approval. The study was considered a feasibility study, and is therefore exempted from registration under FDAAA 801.

Results

As detailed above, the impact of auditory and somatosensory multi-modal stimulation, on outcome measures of chronic tinnitus, was determined by measuring the change in the THI, MML and TLM scores over time. A cohort of 54 participants was recruited as part of this trial, each participant was required to complete 3 intervention free screening assessments and 5 subsequent assessments while using the device.

Two participants dropped out of their own accord. The log files from the devices of six additional participants showed very little use of the device over the study period, <10% compliance. Two additional participants was excluded from analysis; while their corresponding log files showed active use of the device, they did not return for any assessment visits after the V3 assessment. In total ten participants were excluded from the final analysis.

Figure 15:
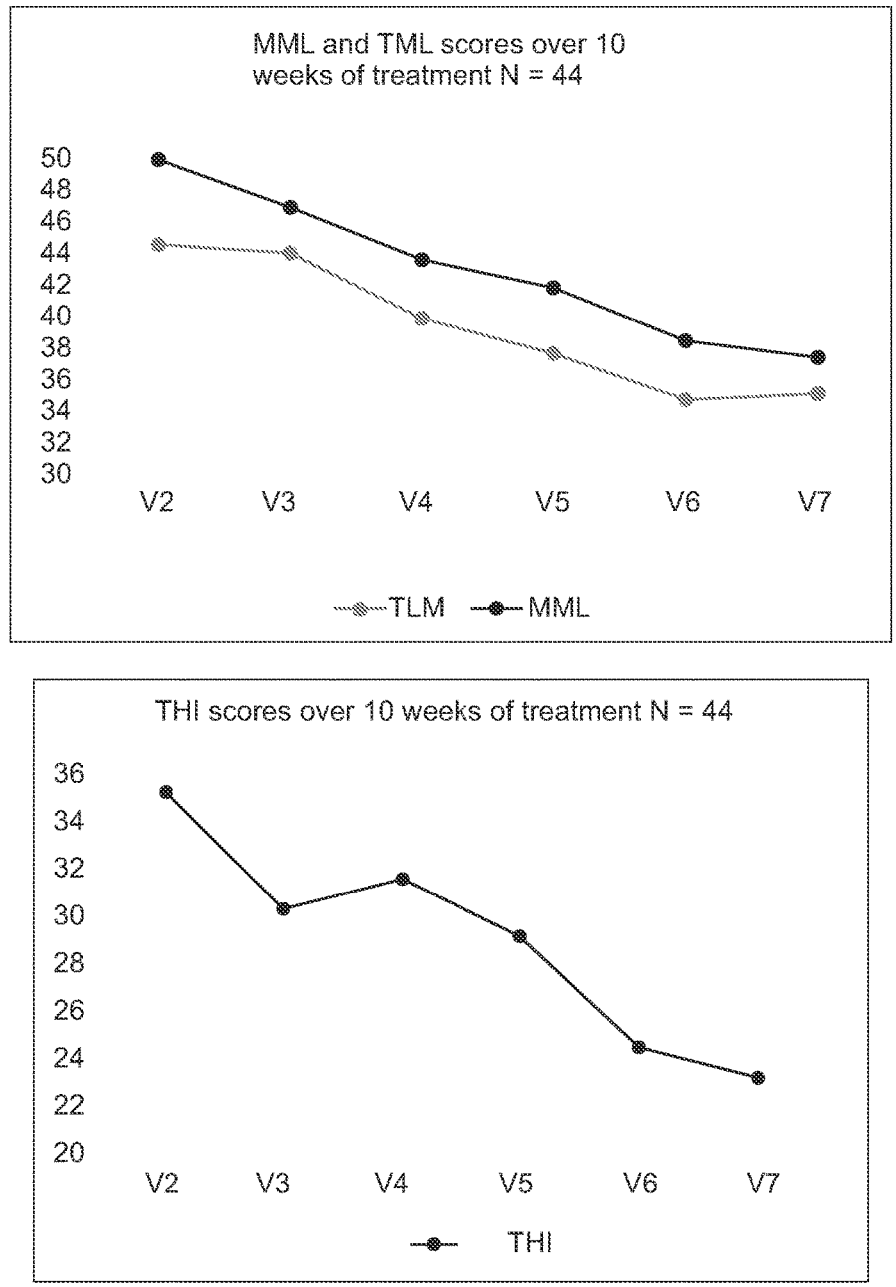
FIG. 15 illustrates performance in response to treatment over a 10 week treatment period in response to clinical trials carried out in accordance with an embodiment of the present invention.
Figure 16:
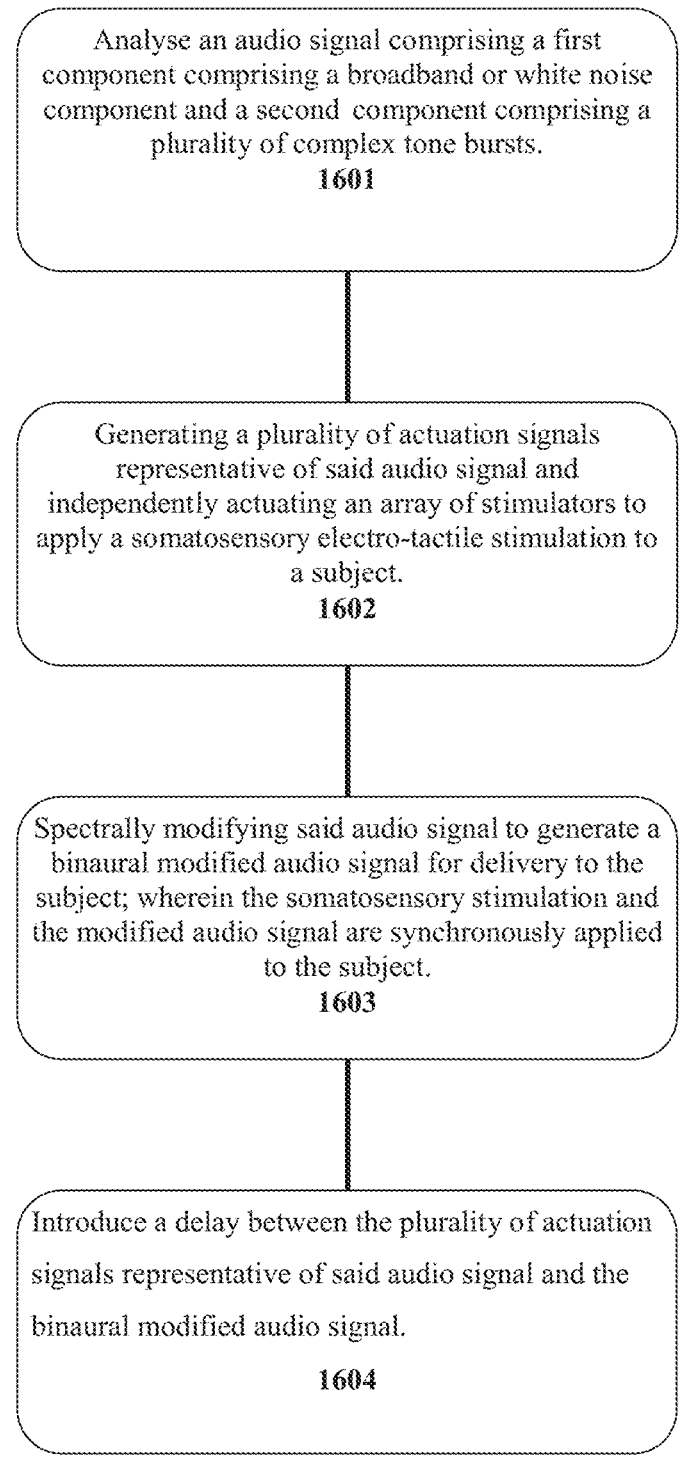
FIG. 16 is a method of treatment in accordance with an embodiment of the present invention.

The symptom scores assessed without intervention at V0, V1 and V2, are employed to better understand variability and improvements in symptoms that may be attributed to non-interventional influences. The average intra-subject coefficient of variance, COV, for the THI, TLM and MML scores over the 3 screening visits, i.e. non interventional monitoring, are 21%, 16% and 13% respectively. Baseline values for analysis were taken from the $3^{rd}$ screening visit, i.e. V2, average and standard variation can be seen in Table 13. Changes in the average THI, TLM and MML scores, for the full cohort over time, are presented in FIG. 15.

TABLE 11 demographic profile of participants.

| | Included in analysis, N = 54 |
|---|---|
| Age | 47.5 ± 11 |
| Men | 34 (63%) |
| Tinnitus type: pure tonal/narrowband | 31 (66%)/16 (34%) |
| Persistence of tinnitus: >2 years/<2 years | 36 (78%)/10 (22%) |
| Tinnitus presence: one ear/both ears | 12 (26%)/34(74%) |
| Tinnitus severity, (VAS)[x] | 6.5 ± 2.2 |
| Tinnitus pitch, (VAS) | 7.1 ± 2.4 |
| Hyperacusis: yes/no | 13 (28%)/41 (72%) |
| Tinnitus type: constant/fluctuate/other | 31(57%)/15(28%)/8(15%) |
| Taking anti-depressant medications | 5 (11%) |

[x]self-rated Visual Analogue Scale, scale 1-10

Table 12 presents the number of participants who achieved clinically significant improvements, as discussed in the analysis section, per symptom, for those that are considered compliant and non-compliant. The highest proportion of improvers are seen on the MML scale, 73% of the 30 participants demonstrating a clinically significant improvement in MML.

TABLE 12 presents the number of improvers/non-improvers for each tinnitus symptom in each compliance class;

|  | Improvers: THI¥ | Improvers: TLM§ | Improvers: MML? |
|---|---|---|---|
| Full Cohort (44) | 20 (45%) | 21(48%) | 28 (64%) |
| Compliant (30) | 17 (57%) | 15 (50%) | 22 (73%) |
| Non-Compliant (14) | 3 (21%) | 6 (43%) | 6 (43%) |

¥Improvers achieve a minimum drop of 7 points on THI scale
§Improvers achieve a minimum drop of 5.3 dB on TLM scale
?Improvers achieve a minimum drop of 5.3 dB on MML scale Table 13, presents the average THI, TLM and MML scores for baseline (V2) and V7 for the full cohort and when the cohort is divided into two classes; compliant and non-compliant.

|  | THI (pts) | | TLM (dB) | | MML (dB) | |
|---|---|---|---|---|---|---|
|  | V2 | V7 | V2 | V7 | V2 | V7 |
|  | (SD) | (SD) | (SD) | (SD) | (SD) | (SD) |
| Full Cohort (44) | 33.7 (24) | 25.1 (20)*** | 42.9 (15) | 37.5 (17) | 47.3 (15) | 39.2 (17)*** |
| Compliant (30) | 35.8 (25) | 24.1 (20)*** | 44.8 (16) | 37.3 (16)*** | 49.0 (15) | 39.2 (18)*** |
| Non-compliant (14) | 29.3 (24) | 27.4 (23) | 38.6 (14) | 37.7 (19) | 43.8 (17) | 39.1 (18) |

Average tinnitus symptom values for baseline and final visit, *p < 0.05, p < 0.01, *p < 0.001

The log files from the device provided information on the usage patterns for stimulation parameters used by the participants. Data from three participants was excluded from this analysis due to errors in the electronic logging system. On the days the device was used, the average session duration for all participants was 47 mins (SD=20 mins). Table 14 presents the usage statistics.

TABLE 14

|  | Average number of compliant days (SD) | Average session duration on day the device used, mins (SD) |
|---|---|---|
| Compliant (30) (*>44 days with session duration >30 mins per day) | 59 (12.3) | 52 (18) |
| Non-Compliant (14) (*<44 days with session duration >30 mins per day) | 33 (9.4) | 33 (17) |

*The average treatment duration across the whole group (N = 44)** was 67 days. Hence a 66% compliance threshold corresponds to 44 days.
** Total number of subjects: 54; Excluded from analysis (10): did not use device (3), drop outs before intervention (3), did not complete assessments schedule (4)

Table 14

The average somatosensory and audio stimulus settings after the first week of use were 6 pt (SD=4.2) (min 0 and max 17) and −8.5 dB (SD=8.1 dB) respectively. The average somatosensory and audio stimulus setting extracted from log files for the final week were 7.4 pts (SD=5.4) and −16 dB (SD=6.6 dB) respectively. There was no statistical difference between the stimulus setting at the beginning and end of treatment. Participants were able to modify the volume of the audio and the intensity of the somatosensory stimulus over the 10 weeks of treatment. From the log data it was observed that participants varied the somatosensory stimulus much more than the audio stimulus; the coefficient of variation was calculated for each participant across the 10 weeks of intervention, the COV across the full cohort was 35% and 15% for somatosensory and auditory stimulus settings respectively. There was no significant relationship established between stimulus settings and changes in symptom scores for either improvers or non-improvers. While no specific assessments of ease of use and tolerability was carried out, no participants reported significant discomfort during assessments at the investigator site.

ADDITIONAL EMBODIMENTS

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be genetically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above. In this respect, it should be appreciated that one implementation of the embodiments of the present technology comprises at least one computer-readable storage medium (e.g., a computer memory, a floppy disk, a compact disk, a tape, a flash drive, etc.) encoded with a computer program (i.e., a plurality of instructions), which, when executed on a processor, performs the above-discussed functions of the embodiments of the present technology. The computer-readable storage medium can be transportable such that the program stored thereon can be loaded onto any computer resource to implement the aspects of the present technology discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology.

While various inventive embodiments have been described and illustrated herein, those of ordinary skill in the art will readily envision a variety of other means and/or structure for performing the function and/or obtaining the results and/or one or more of the advantages described herein, and each of such variations and/or modifications is deemed to be within the scope of the inventive embodiments described herein. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present technology are directed to each individual feature, system, article, material, kit, and/or method described herein. In addition, any combination of two or more such features, systems, articles, materials, kits, and/or methods, if such features, systems, articles, materials, kits, and/or methods are not mutually inconsistence, is included within the inventive scope of the present disclosure. All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternative (i.e., "one or the other but not both") when preceded by terms of exclusivity, such as "either," "one of," "only one of," or "exactly one of." "Consisting essentially of," when used in the claims, shall have its ordinary meaning as used in the field of patent law. As used herein the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than, B (and optionally including other elements); etc. It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. The words "comprises/comprising" and the words "having/including" when used herein with reference to the present invention are used to specify the presence of stated features, integers, steps or components but does not preclude the presence or addition of one or more other features, integers, steps, components or groups thereof. It is appreciated that certain features of the invention, which are for clarity, described in the context of separate embodiments, may also be provided in combination in a single embodiment. Conversely, various features of the invention which are, for brevity described in the context of a single embodiment, may also be provided separately or in any suitable combination.

The invention claimed is:

1. An apparatus for use in treating a neurological disorder of the auditory system, comprising a stimulus generation unit and a somatosensory stimulation unit; the stimulus generation unit operable to receive an audio signal and analyse the audio signal, said audio signal comprising a first component comprising a broadband or white noise component and a second component comprising a plurality of complex tone bursts, and generate a plurality of actuation signals representative of at least one of the first or second component of said audio signal and further to spectrally modify said audio signal to generate a binaural modified audio signal for delivery to a subject; and wherein said somatosensory stimulation unit comprises:

an array of stimulators each of which can be independently actuated to apply a somatosensory stimulation to the subject with the modified audio signal, and an input for receiving the plurality of actuation signals from said stimulus generation unit and directing individual actuation signals in a predetermined pattern to individual stimulators in the array, the stimulus generation unit being further configured to introduce a delay between the plurality of actuation signals representative of said audio signal and the binaural modified audio signal wherein the delay is a fixed delay in a range −50 ms to +50 ms or wherein the delay is a random delay between the modified audio signal and the plurality of actuation signals, said random delay having a rectangular probability density function with limits up to +/−50 ms, or having a Gaussian probability density function with standard deviation up to 20 ms.

2. The apparatus according to claim 1 wherein the stimulus generation unit is operable to schedule the plurality of actuation signals over a predetermined period wherein the plurality of actuation signals scheduled over the predetermined period is proportional to an amplitude of the binaural modified audio signal within a plurality of critical band frequencies and within said predetermined period.

3. The apparatus according to claim 2 wherein the predetermined period is 23.2 ms or wherein the predetermined period is set such that the plurality of actuation signals occur having a period of at least one somatosensory nerve fibre refractory period between each of said actuation signals.

4. The apparatus according to claim 1 wherein the stimulus generation unit comprises an amplitude control for controlling an amplitude of the modified audio signal and an amplitude of the somatosensory stimulation.

5. The apparatus according to claim 4 wherein the amplitude control is further operable to modulate the amplitude of the modified audio signal for an interval during a treatment session of the subject.

6. The apparatus according to claim 5 wherein the amplitude control is operable to ramp an amplitude of the modified audio signal from a nominal level down to a level commensurate with a hearing level of the subject for between 1 minute and 5 minutes before completion of a treatment session of the subject.

7. The apparatus according to claim 1 wherein the stimulus generation unit further comprises a band boost filter calibrated in accordance with an audiogram of the subject and wherein the stimulus generation unit is operable to spectrally modify said audio signal by passing the audio signal through said band boost filter to produce said modified audio signal.

8. The apparatus according to claim 7 wherein the band boost filter is a band boost filter with centre frequency set to match a steepest roll off of the audiogram of a patient, wherein a half-power bandwidth of the band boost filter is between 0.5 and 1.5 octaves normalised to the centre frequency, and with a boost magnitude of at least 12 dB.

9. The apparatus according to claim 7 wherein the band boost filter is representative of an inverse of the audiogram of the subject in an ipsilateral ear and the filter is configured to compensate for deficits of at least 30 dB and operable in a range from 500 Hz to 16 kHz.

10. The apparatus according to claim 1 wherein said array of stimulators comprises an additional array comprising at least two stimulators, symmetrically arranged relative to the array of stimulators and configured to deliver a pseudo-stimulus to the subject.

11. The apparatus according to claim 10 wherein the somatosensory stimulation comprises a periodic pulse train having a pulse train with a period less than a repolarisation period of a nerve fibre to which the somatosensory stimulation unit is applied.

12. The apparatus according to claim 11 wherein the somatosensory stimulation unit is a body dimensioned to be applied to a mandibular branch or a lingual branch or a maxillary branch or an ophthalmic branch of the trigeminal nerve, or to an accessory nerve or cervical spinal nerves, C1 and C2.

13. The apparatus according to claim 1 wherein the array of stimulators is arranged to deliver both a treatment stimulus and a pseudo stimulus, such that both stimuli are multiplexed in time with a mark:space ratio of pseudo to treatment stimulus of no more than 0.1.

14. The apparatus according to claim 1 wherein said somatosensory stimulation unit is a body dimensioned to be applied trans-cutaneously or trans-mucosally over a nerve fibre of the subject.

15. The apparatus according to claim 14 wherein the somatosensory stimulation unit is a body dimensioned to be applied to a mandibular branch or a lingual branch or a maxillary branch or an ophthalmic branch of the trigeminal nerve, or to an accessory nerve or the cervical spinal nerves, C1 and C2.

16. The apparatus according to claim 1 wherein somatosensory unit is a body dimensioned to be located on a tongue and wherein the array of stimulators comprises a split array having an equal number of stimulators distributed along a medial line of the tongue and wherein the predetermined pattern comprises an ipsilateral mapping of the individual actuation signals with a dead band located along the medial line.

17. The apparatus according to claim 16 wherein the somatosensory unit is further dimensioned to provide a positioning aid for centring the somatosensory unit along the medial line.

18. The apparatus according to claim 1 wherein the array of stimulators are arranged in a raster pattern such that each stimulator in the raster pattern is arranged from lowest frequency bin to highest frequency bin or the array of stimulators is arranged in a spiral pattern having a lowest frequency mapping on an inside of the spiral with the highest frequency on an outside of the spiral.

* * * * *